United States Patent
Ohta et al.

(10) Patent No.: US 8,809,048 B2
(45) Date of Patent: Aug. 19, 2014

(54) PLASMID VECTOR

(75) Inventors: Yukari Ohta, Kanagawa (JP); Yuji Hatada, Kanagawa (JP); Kozue Mori, Kanagawa (JP); Nobuyuki Nakamura, Kanagawa (JP)

(73) Assignee: Independent Administrative Institution, Japan Agency for Marine-Earth Science and Technology, Yokosuka-shi (JP)

( * ) Notice: Subject to any disclaimer, the term of this patent is extended or adjusted under 35 U.S.C. 154(b) by 0 days.

(21) Appl. No.: 13/637,945

(22) PCT Filed: Mar. 18, 2011

(86) PCT No.: PCT/JP2011/056635
§ 371 (c)(1),
(2), (4) Date: Sep. 27, 2012

(87) PCT Pub. No.: WO2011/125467
PCT Pub. Date: Oct. 13, 2011

(65) Prior Publication Data
US 2013/0084621 A1    Apr. 4, 2013

(30) Foreign Application Priority Data
Mar. 31, 2010    (JP) .................................. 2010-081774

(51) Int. Cl.
*C12N 15/00*    (2006.01)
*C12N 1/00*    (2006.01)
*C12N 1/20*    (2006.01)
*C12P 21/04*    (2006.01)
*C12P 21/06*    (2006.01)

(52) U.S. Cl.
USPC ...... 435/320.1; 435/69.1; 435/71.1; 435/243; 435/252.1; 435/252.2; 435/252.3

(58) Field of Classification Search
None
See application file for complete search history.

(56) References Cited

U.S. PATENT DOCUMENTS

2012/0142050 A1 *    6/2012    Matsumura et al. ......... 435/69.1

FOREIGN PATENT DOCUMENTS

JP      2002-112790 A       4/2002
WO      WO 2010/082572 A1   7/2010

OTHER PUBLICATIONS

Zhong et al., "A 50-kb Plasemid Rich in Mobile Gene Sequences Isoated from a Marine Micrococcus" 47 Plasmid 1-9 (2002).*
Chattoraj et al. "P1 plasmid replication: Multiple functions of RepA protein at the origin" 82 Proceedings of the National Academy of Sciences USA 2588-2592 (1985).*
Kocur et al., "The Genus Micrococcus" 3 Prokaryotes 961-971 (2006).*
Mathis et al., "Isolation and Characterization of Micrococcus Plasmids" 10 Current Microbiology 339-344 (1984).*
Martin et al., "Molecular, technological and safety characterization of Gram-positive catalase-positive cocci from slightly fermented sausages" 107 International Journal of Food Microbiology 148-158 (2006).*
Verma et al. "An Economical Large-Scale Procedure to Purify Micrococcus Plasmid DNA" 6(10) BioTechniques 936-940 (1988).*
Aymerich et al., "Microbial Quality and Direct PCR Identification of Lactic Acid Bacteria and Nonpathogenic Staphylococci from Artisinal Low-Acid Sausages" 69(8) Applied and Environmental Microbiology 4583-4594 (2003).*
Kim et al., "*Kocuria marina* sp. nov., a novel actinobacterium isolated from marina sediment," International Journal of Systematic and Evolutionary Microbiology (2004) vol. 54. pp. 1617-1620.
Takarada et al., "Complete Genome Sequence of th Soil Actinomycete *Kocuria rhizophila*." Journal of Bacteriology (Jun. 2008), vol. 190, No. 12, pp. 4139-4146.

* cited by examiner

*Primary Examiner* — Jennifer Dunston
*Assistant Examiner* — Nancy J Leith
(74) *Attorney, Agent, or Firm* — Birch, Stewart, Kolasch & Birch, LLP

(57) ABSTRACT

The object is to provide a technique for modifying a bacterium belonging to the genus *Kocuria* through genetic engineering for industrially effectively utilizing the bacterium belonging to the genus *Kocuria*. The above object can be achieved by providing a cyclic plasmid, which has a replication region comprising the base sequence of a DNA-binding protein-like protein gene, the base sequence of a replicase-like protein gene, and the base sequence represented by SEQ ID NO:45, and is autonomously replicable in bacteria. As an example of the aforesaid plasmid, a plasmid containing a base sequence represented by SEQ ID NO:3 or 4 which originates in *Kocuria* sp. MBE131 strain (FERM P-21885) can be cited.

4 Claims, 11 Drawing Sheets

FIG.2 (SEQ ID NO: 4)

```
          10        20        30        40        50        60        70        80        90
ATAAGCCCAAGGTGAGGGGACGCTCCCGGGGCCTCTCAGCCCCCCTCTGAGGGCTCCTGCGGGCACCTCCTACGATCCTCCGAACAGCC
         100       110       120       130       140       150       160       170       180
CTGATCGTCACACCTCATGCATCATTCGATGAGCCAGGTCTAGGTGACCAAACGCAGGCGGCCACAGACTCAGCTGCACTCTCATCGTGA
         190       200       210       220       230       240       250       260       270
GGTGCCCAGAGCGTCGCAACAAGGCACCGACCCAGCCTCAATTTTCATCCGCCGGCCTTAACGGCGACCGTCACTGTTGATGACTTTGC
         280       290       300       310       320       330       340       350       360
TGTCCTCGAATCACCCTTCGCGGGTGAGGGGTAACCCGCTTCGGGTGAGGCAACCAGAACGGGTCCCTGTGCTCGGCTATGTGGTCGAGC
         370       380       390       400       410       420       430       440       450
AGGGTGCCTGGTGGGGTGGCGTGGTCGTTGTCGGCGGGCCGGTTTCGGGCGCGCTGGGGTGACCTAGCTgtgcgcacCGAGGacggtgCG
         460       470       480       490       500       510       520       530       540
AAGGACAAGATGAGCGTCTTTCCCGAGggccggccAAAGAATGCAAGAGGTGTGACGACTTGGATCAGAGTtcggagctccgaCGCATTG
         550       560       570       580       590       600       610       620       630
GGAGGTGATTGGGTGCAGCGTGAGACCAGTCCGTAGCGTTTGACGAATGCAAATGCGACGCGGGGACCAGGAGGCTAGACATCGTCGAGA
         640       650       660       670       680       690       700       710       720
TATGGCTTGGATTCTGGTGCTGCTGGCTGGAGTGCAGGTGGGTTTGCTGGCGACGGTGATCGGTGTCTTGGTCGAGGACCTCGTGGTGGG
         730       740       750       760       770       780       790       800       810
CACTGTCGTTGCTTTGGTTCCTGGGGCTGTGGTGGTGGGGCTGTGGTGGCGGCGGTTTTTGGACTAGCGCGGCGTTGCTGGGCATGGAAAA
         820       830       840       850       860       870       880       890       900
AGCCGGGCTGCTGCCCGGCTTTTTCTTCTGGGAGGCGGGGCCTGGTCAACCGGGCCtcccgggaAGCGGTGGTGTGAGCACGTCAGTTCC
         910       920       930       940       950       960       970       980       990
CGCCTCCAGTGTTGGCCGTTCTTCGGTTTGTTCCCAAAAGTGACGGCGATGGGTGGGTGGAAGGTCCCGTCCAGGTCTGATTtgccggca
        1000      1010      1020      1030      1040      1050      1060      1070      1080
caggtTGCTGGGCCGGGGTTGTCCCCGTAGGGGTCTGTCCCGGTCAGGCTGGACGGTGCGTGGTCATAAACCGTGGGTCGGTTCGGAGAG
        1090      1100      1110      1120      1130      1140      1150      1160      1170
CCGGGGGGTGCTTCCTATCGTCGTGAGATGAGCAGAGAACGCTATGAGCCGATGAGTGAGGCCCGGTTGGAAGTCGCTTGGATGGTCGT
        1180      1190      1200      1210      1220      1230      1240      1250      1260
GTTGCTGGGGTGTGCGCTGGTTCTTATGGGTGGGTGGCCCTGGATGTGTtgatcgatcaTCTCGCTGTCAGCTTCGCCTTGGCGGGGGT
        1270      1280      1290      1300      1310      1320      1330      1340      1350
GCCGAGTGTGTTGGTGGTGGCGGTGTTGTGGCGGCGgcacgtgcGCTAAGCCGTGTACGGGCACAGAAAAAGCCGGTGGTAGAGCCCGG
        1360      1370      1380      1390      1400      1410      1420      1430      1440
CTTTTTCCGTGGGGGAGAGTCTCGTACCCCGCGTCTCAGTGTCCTGCAaccggtCGTGATGCCTACTGCCGCTACACGGAGCAAAGCTA
        1450      1460      1470      1480      1490      1500      1510      1520      1530
TGCGTTATGTGCCATAAACGCGGATCGCCCTTCGTCCAGCTCGTGGAGCTGGCTGAGTGCCTATGTGCCATAGGCGGCGGGGGCACCCC
        1540      1550      1560      1570      1580      1590      1600      1610      1620
AGCGGGCTCGTGTGAGCGCTGCGCTGGGCATAGGGAAGGCCGGGCGCTAGCCCAGCCCTCCATGGGGGCAGAGGGCCCCGTGGTGTTGAG
        1630      1640      1650      1660      1670      1680      1690      1700      1710
AGTGGCGAGCCCTACTGAGGGTCCTCGAAGGCGTCGGGGGCGCTTCGTGTCCTCTTCAGTTTTTGATCCCTGGCGTCCTGAACTTCGTTC
        1720      1730      1740      1750      1760      1770      1780      1790      1800
GCGACTGCCTCCGGGGTGCCGGTGGCAAGGAGAGCATGCACATGGGCGACCCTCAGCTTGTAATGGGCTTTTTCCAGGTCTTCCTTCGTG
                                         M   G   D   P   O   L   V   M   G   F   F   Q   V   F   L   R   A
                                         ORF1  SEQ ID NO:
        1810      1820      1830      1840      1850      1860      1870      1880      1890
CCTTTCTCGTACAGAGCGTCTGCTTCGAGAAGGGCCCATTCCGCTTCGACAAACTGCCGGGCAAGAAGTTTTTTGCTGGATGGCTAGTC
    F   L   V   Q   S   V   C   F   E   K   G   P   F   R   F   D   K   L   P   G   K   K   F   A   G   W   L   S   H
        1900      1910      1920      1930      1940      1950      1960      1970      1980
ATGGCAAGGAACGTAGCTGCCGAAGTAGTGAAGGCTGTACAGATCCGACGGGGTTCGCGCGGGTCCGTCAGTAGGCCAGTGATGGGCCAT
    G   K   E   R   S   C   R   S   S   E   G   C   T   D   P   T   R   F   A   R   V   R   Q   *
        1990      2000      2010      2020      2030      2040      2050      2060      2070
AGGGTGACCAGGAAAGAGTTGAGCCCCGGAGATTCCACCCTCCGGGGCTCGACTTCCCCGATTGATAGCGGCAATCAGGAGAAGCCTTGT
                                                                                        M
                                                                               SEQ ID NO: 5   ORF2
        2080      2090      2100      2110      2120      2130      2140      2150      2160
GACCAGTGTAGGCACGCACCTTCCCTCGTCCACCAGCCCCGCCGCAACACGGCAGGCGGCTGTTCGGCAGGCATTTGTTAACCATTTAGG
    T   S   V   G   T   H   L   P   S   S   T   S   P   A   A   T   R   Q   A   A   V   R   Q   A   F   V   N   H   L   G
```

FIG. 3 (SEQ ID NOS: 4 and 5, cont'd.)

```
         2170      2180      2190      2200      2210      2220      2230      2240      2250
CGTGCGCCACGTGCGTGTGGCGGCCACCAAGAACGGTGCGCCGCGCACCGTTCCCATTGAGGCGTTAGGCGAGTTCGCCTTTTGGACGCC
  V  R  H  V  R  V  A  A  T  K  N  G  A  P  R  T  V  P  I  E  A  L  G  E  F  A  F  W  T  P 2260      2270      2280      2290      2300      2310      2320      2330      2340
ACCGGCCTGGCCCAACCTCGGATTGCTGACTATTGACGTCGACCGGGATGCGGCCGTGCTCGAGCTCTTCGCCGCCCCTGCCCTGCCGCA
  P  A  W  P  N  L  G  L  L  T  I  D  V  D  R  D  A  A  V  L  E  L  F  A  A  P  A  L  P  H 2350      2360      2370      2380      2390      2400      2410      2420      2430
TGTGGTCGTGGAGACCCCCGCGGGGCCCAAGCGGTGTGGCTGATCGACCGAGTACACACCGGCCCGAACGCCCGCCCGCACCCGATCGC
  V  V  V  E  T  P  R  G  A  Q  A  V  W  L  I  D  R  V  H  T  G  P  N  A  R  P  H  P  I  A 2440      2450      2460      2470      2480      2490      2500      2510      2520
CTATGCCGAAACCGTAGGAAGCGCTTTGCGTGCCTCCCTGGATGGAGACTCGGCCGTGGATCCATTGCGCCCGGTACGTACCCGTAACCC
  Y  A  E  T  V  G  S  A  L  R  A  S  L  D  G  D  S  A  V  D  P  L  R  P  V  R  T  R  N  P 2530      2540      2550      2560      2570      2580      2590      2600      2610
CTGCTACAGACCTGCACAGCGCGATGTGTTCACCACTGCCCGCCCGCTAACGGCGCCCTACCGTCTCGGAGAGCTCCAGAAATCCCTGGA
  C  Y  R  P  A  Q  R  D  V  F  T  T  A  R  P  L  T  A  P  Y  R  L  G  E  L  Q  K  S  L  D 2620      2630      2640      2650      2660      2670      2680      2690      2700
TGCTGCTGGAGCATGGCCAACACGTCCTGAGCGCTCTCAGGCCCGTGGAAGGGCGCAGAAGGCCGTTGACGGAGTGTTCGTGGGCCGTAA
  A  A  G  A  W  P  T  R  P  E  R  S  Q  A  R  G  R  A  Q  K  A  V  D  G  V  F  V  G  R  N 2710      2720      2730      2740      2750      2760      2770      2780      2790
CGACGCCGTCAACCGCTCCACCTGGCTGACCGTGCGCTACGGACTCGAAAATGGTTCCGTGACTCACTGGACCGATGCCGACGTGCTGGA
  D  A  V  N  R  S  T  W  L  T  V  R  Y  G  L  E  N  G  S  V  T  H  W  T  D  A  D  V  L  E 2800      2810      2820      2830      2840      2850      2860      2870      2880
GCTGGCCCATGGCATTAACGAGGCCGTCGCTGCTGAGCAAGGCGTGCCGCCCTTACCCGAGGATCAAGTGCGCGACTTGGCTGTCTCGAT
  L  A  H  G  I  N  E  A  V  A  A  E  Q  G  V  P  P  L  P  E  D  Q  V  R  D  L  A  V  S  I 2890      2900      2910      2920      2930      2940      2950      2960      2970
CTGCCGGCATCAACACCGACCTGGCCGCCGAGCCATCTCCGGACAAGGCTCGGCCACCGCCCGCGCCCTCGGCGCTAAAGGCGGCGCAGC
  C  R  H  Q  H  R  P  G  R  R  A  I  S  G  Q  G  S  A  T  A  R  L  G  A  K  G  G  A  A 2980      2990      3000      3010      3020      3030      3040      3050      3060
CCGTTCCGAGGCCAAAACCATTAGCGGGCGGCGCAACGTGGGCAAGGCGACCGCTGTGCGTTCCGCATCCGCGGCCTTGCGTTCTGAGAG
  R  S  E  A  K  T  I  S  G  R  R  N  V  G  K  A  T  A  V  R  S  A  S  A  A  L  R  S  E  S 3070      3080      3090      3100      3110      3120      3130      3140      3150
CATCCGAATCCTGGCCGAGCAAGGCACACCTACGAGGCCATTGCCGCCGCTGTCGGATGCTCCACTAAGACCGTTCAGCGTGCTCTTCG
  I  R  I  L  A  E  Q  G  H  T  Y  E  A  I  A  A  V  G  C  S  T  K  T  V  Q  R  A  L  R 3160      3170      3180
CGACCTCTGAAACAGTCTCCGTCGAGGTGGACATTTC
  D  L  *
```

FIG.11A

>>CP001630|CP001630.1 Actinosynnema mirum DSM 43827, com (8248144 nt)

initn: 86 init1: 86 opt: 264 Z-score: 225.8 bits: 61.7 E(): 1.7e-05 banded Smith-Waterman score: 285; 53.889% identity (53.889% similar) in 900 nt overlap
(1195-2046:1317925-1318781)

```
                    1170      1180      1190      1200      1210      1220
1135-2046 of SEQ
                pKR100 CGCCACGTGCGTGTGGCGGCCACCAAGAACGGTGCGCCGCGCACCGTTCCCATTGAGGCG
ID NO: 3
                         :  : :::: :::   :::  :::   :   :::
SEQ ID NO: 70   CP0016 ACGTCGCCGCGCTCGTCCCGTCCGGGTTCGGCTCCGCCTCGC-TCGTGCCC---GCCGCG
                       1317900    1317910   1317920    1317930   1317940     1317950

1230      1240      1250      1260      1270      1280
                pKR100 TTAGGCGAGTTCGCCTTTTGGACGCCACCGGCCTGGCCCAACCTCGGATTGCTGACTATT
                       ::  ::::  :  :::  :     :::::::: :::::   ::   ::    :  :::
                CP0016 TTCGGCGTCTCCGCACT-----CGCCACCGACCTGGATC---CCGCAGACCTC-GAC----
                           1317960      1317970   1317980    1317990

1290      1300      1310      1320      1330      1340
                pKR100 GACGTCGACCGGGATGCGGCCGTGCTCGAGCTCTTCGCCGCCCCTGCCCTGCCGCATGTG
                        ::   ::   :::   :  :::: :  :::      :::::::  ::  :::   ::  ::
                CP0016 CCCGCCGCCCTGGACCCCGCCGAGGTCGCCGGGCTCGCCGCGCCCGAGCTGGGGGAGCTG
                       1318000    1318010   1318020    1318030    1318040   1318050

1350      1360      1370      1380      1390      1400
                pKR100 GTCGTGGAGACCCCCCGCGGGGCCCAAGCGGTGTGGCTGA--TCGACCGAGTACACACCG
                         :    :   :  ::  :::::  ::  :  ::: :  :::  ::  ::  ::  :   :  :::
                CP0016 --CTGCGCCTGCGCCTGCGGGTCCGACCCGGCGCGGCCGAGGTGGTGCGGGCGACCGCCG
                         1318060     1318070    1318080     1318090    1318100     1318110

1410      1420      1430      1440      1450
                pKR100 GCC----CGA--ACGCCCGCCCGCACCCGATCGCCTATGCCGAAACCGTAG-GAAGCGCT
                       ::    :::   :::::   :    :::  :     :    : :   :::  :   :   :::
                CP0016 TCCTCGGCGAGGACGCCACCGTCGACCGGGTCGCCGAGCTGGCAGGCGTCGAGCACCGC-
                           1318120    1318130    1318140    1318150    1318160    1318170

1460      1470      1480      1490      1500      1510
                pKR100 TTGCGTGC-CTCCCTGGATGGAGACTCGGCCGTGGATCCATTGCGCCCGGTACGTACCCG
                       ::::  : ::::::   :  : :   ::  :   :      :::  ::   :   : ::::
                CP0016 -GAGGTGCTCGCCCTGGTCGACGCCCTGGTCCGGCTGCGCCTGCTCCGCGACGGCACCCC
                        1318180     1318190    1318200    1318210    1318220     1318230
```

FIG.11B

```
                1520       1530       1540       1550       1560       1570
1135-2046 of SEQ  pKR100  TAACCCCTGCTACAGACCTGCACAGCGCG-ATGTGTTCACCACTGCCCGCCCGCTAACGG
ID NO: 3
                          : ::: : ::    ::    : ::: :  :: :: : :  : :: ::: :    ::
SEQ ID NO: 70    CP0016  GCTCGCCTTCAACCACCCCTACCTGCGGGCCTGCGTGCTCGCCGACCTGCCGG---TCGC
                        1318240    1318250    1318260    1318270    1318280      1318290
                        1580       1590       1600       1610       1620       1630
                 pKR100  CGCCCTACCGTCTCGGAGAGCTCCAGAAATCCCTGGATGCTGCTGGAGCATGGCCAACAC

: :::   :: : : ::    : :: :      ::: : :::    :::    :: ::: :
                 CP0016  CACCC--GCGCCGCCGACCACGCCCGCGCCGCCTCGGCGCTCGCCGAGGCCGGGGAAC-C
                          1318300    1318310    1318320    1318330    1318340
                        1640       1650       1660       1670       1680
                 pKR100  GTCCTGAGCGCTCTCAG-GCCCGTG-GAAGGGCGCA-GAAG-GCCGTTGAC--GGAGTGT

: :: :   : :: : :  :: : :: :  ::: :: :: : :::: :: :  :: : ::
                 CP0016  GGCCAGGCGGGTCGCCGCGCACCTGCGCCAGGCCCACGACGTGCCGCTGCCCTGGGGCGT
                        1318350    1318360    1318370    1318380    1318390    1318400
                        1690       1700       1710       1720       1730       1740
                 pKR100  TCGTGGGCCGTAACGACGCCGTCAACCGCTCCACCTGGCTGACCGTGCGCTACGGACTCG

: : :: :   :::  ::::    ::::::   :::   ::  : :: ::       ::
                 CP0016  CCCGGTGCTG-CGCGAGGCCG---CCCGCTCGGC---GCTGCGCGCGGGCGACCCGGCCG
                        1318410    1318420    1318430    1318440    1318450    1318460
                        1750       1760       1770       1780       1790       1800
                 pKR100  AAAATGGTTCCGTGACTCACTGGA----CCGATGCCGACGTGC-TGGAGCTGGCCCATGG

:      :  ::: : ::  :::::    :: ::: :   ::     : ::  ::: : :
                 CP0016  A------GGCCCGCGCCTGTCTGGAGCGCGCGCTGCGGGAGCGCGCCGCGCCCGCCGAGCG
                                1318470    1318480    1318490    1318500    1318510
```

FIG.11C

```
                         1520       1530       1540       1550       1560       1570
1135-2046 of SEQ  pKR100 TAACCCCTGCTACAGACCTGCACAGCGCG-ATGTGTTCACCACTGCCCGCCCGCTAACGG
ID NO: 3
                         : ::: : ::    ::     : ::: :   :: ::  : :   :  ::  ::: :     ::
SEQ ID NO: 70     CP0016 GCTCGCCTTCAACCACCCCTACCTGCGGGCCTGCGTGCTCGCCGACCTGCCGG---TCGC
                       1318240    1318250    1318260    1318270    1318280    1318290
                         1580       1590       1600       1610       1620       1630
                  pKR100 CGCCCTACCGTCTCGGAGAGCTCCAGAAATCCCTGGATGCTGCTGGAGCATGGCCAACAC
                         : :::    ::  :  : ::    :  :: :         ::: :  :::     :::    :: ::: :
                  CP0016 CACCC--GCGCCGCCGACCACGCCCGCGCCGCCTCGGCGCTCGCCGAGGCCGGGGAAC-C
                       1318300   1318310    1318320    1318330    1318340
                         1640       1650       1660       1670       1680
                  pKR100 GTCCTGAGCGCTCTCAG-GCCCGTG-GAAGGGCGCA-GAAG-GCCGTTGAC--GGAGTGT
                         : :: :      : ::  : :: :  :: :     ::: :: :: : :::: ::  :  :: : ::
                  CP0016 GGCCAGGCGGGTCGCCGCGCACCTGCGCCAGGCCCACGACGTGCCGCTGCCCTGGGGCGT
                       1318350   1318360    1318370    1318380    1318390    1318400
                         1690       1700       1710       1720       1730       1740
                  pKR100 TCGTGGGCCGTAACGACGCCGTCAACCGCTCCACCTGGCTGACCGTGCGCTACGGACTCG
                         :   : ::  :    ::: ::::   ::::::  :   ::::  :: : :: ::         ::
                  CP0016 CCCGGTGCTG-CGCGAGGCCG---CCCGCTCGGC---GCTGCGCGCGGGCGACCCGGCCG
                       1318410    1318420    1318430    1318440    1318450    1318460
                         1750       1760       1770       1780       1790       1800
                  pKR100 AAAATGGTTCCGTGACTCACTGGA----CCGATGCCGACGTGC-TGGAGCTGGCCCATGG
                         :         :  ::: : ::  :::::    :: :::  :  : ::   : ::   ::: :  :
                  CP0016 A------GGCCCGCGCCTGTCTGGAGCGCGCGCTGCGGGAGCGCGCCGCGCCCGCCGAGCG
                              1318470    1318480    1318490    1318500    1318510
```

PLASMID VECTOR

CROSS-REFERENCE TO RELATED APPLICATION

The present application claims priority from Japanese Patent Application No. 2010-81774 filed on Mar. 31, 2010, the entire disclosures of which are incorporated herein by reference.

TECHNICAL FIELD

The present invention relates to a technique that contributes to improving a function of a microorganism with the use of genetic engineering techniques. More specifically, the present invention relates to a plasmid vector derived from bacteria of the genus *Kocuria*.

BACKGROUND ART

Many bacteria of the family Micrococcaceae have been recognized to be effective in food industry, pharmaceutical industry, chemical industry, environmental cleanup, and other fields. For example, in producing dairy products such as cheese or in other fields, propionibacteria are used. As L-glutamine-producing microorganisms, bacteria of the genus *Brevibacteria* are known.

However, wild-type strains of the above bacteria have various problems such as the lower ability to generate products and the difficulty to culture the bacteria. To solve such problems, attempts have been made to obtain variant strains that have the improved ability to generate products and adjust to the environment, among other things, through genetic manipulation of the bacteria. Among those used for the manipulation are vectors such as plasmids, which are autonomously replicable in the bacteria. For example, one of the vectors available to propionibacteria is disclosed in Patent Publication 1, JP 2002-112790 A (the disclosures of Patent Publication 1 are incorporated herein by reference).

Among the bacteria belonging to the family Micrococcaceae, bacteria of the genus *Kocuria* are known. Bacteria of the genus *Kocuria* show high levels of organic solvent tolerance, heavy metal resistance, and proliferating ability, and are expected to be used in various fields, such as production of fuel and pharmaceutical chemical products, and environmental cleanup.

DISCLOSURE OF THE INVENTION

Problem to be Solved by the Invention

However, the techniques to retain a foreign gene in a stable manner in bacteria of the genus *Kocuria* remain unknown. There is no case of successfully modifying microorganisms with the use of the above bacteria by means of genetic engineering techniques. As a result, it is not possible to add new biological functions, or to optimize the original functionality. Therefore, few bacteria of the genus *Kocuria* are used in the industrial world.

In the present invention, the problem to be solved by the invention is therefore to provide a technique to modify bacteria of the genus *Kocuria* in a genetic engineering manner in order to make possible effectively industrial use of bacteria of the genus *Kocuria*.

Means for Solving the Problem

As a result of intensive studies to solve the above problem, the present inventors have succeeded in isolating, from bottom sediment at a depth of about 2,000 meters in Sagami Bay, *Kocuria* sp. strain MBE131 (FERN P-21885; also referred to as strain MBE131, hereinafter), which is a new bacterium of the genus *Kocuria* having a circular plasmid that is relatively small in size and easy to handle.

The present inventors named a plasmid acquired from the strain MBE 131 pKR100, and combined pKR100 with a foreign gene and a plasmid that is autonomously replicable in *Escherichia coli* to constitute a shuttle vector for the strain MBE 131 and *Escherichia coli*. After the shuttle vector was introduced into the strain MBE 131 and *Escherichia coli*, the foreign gene was expressed in each of them.

As a result of further studies on plasmid pKR100, the present inventors discovered a region (replication region) that is predicted to play a role in DNA replication in plasmid pKR100. Then, the present inventors prepared recombinant plasmids that have a foreign gene inserted into a different region from the replication region of plasmid pKR100, and introduced the recombinant plasmids into *Kocuria rhizophila* DC2201 strain (NBRC103217), which is a bacterium of the genus *Kocuria* different from the strain MBE 131. As a result, the recombinant plasmids expressed the foreign gene and were autonomously replicable even in *Kocuria rhizophila* DC2201 strain.

The present invention has been successfully accomplished based on the above findings. According to the present invention, there is provided a circular plasmid that is autonomously replicable in bacteria, having a replication region comprising a base sequence of a DNA-binding protein-like protein gene; a base sequence of a replicase-like protein gene; and a base sequence disclosed in SEQ ID NO: 45, or a base sequence that hybridizes under stringent conditions to a base sequence complementary to the base sequence.

According to another aspect of the present invention, there is provided a circular plasmid that is autonomously replicable in bacteria, having a replication region comprising a base sequence of a DNA-binding protein-like protein gene; a base sequence of a replicase-like protein gene; and at least one sequence selected from a group consisting of a DNA-binding protein binding sequence and a repeat motif sequence.

According to another aspect of the present invention, there is provided a circular plasmid that is autonomously replicable in bacteria, having a replication region comprising a base sequence of a DNA-binding protein-like protein gene; a base sequence of a replicase-like protein gene; and a base sequence comprising at least one sequence selected from a group consisting of a DNA-binding protein binding sequence and a repeat motif sequence, an oxidant sensitive sequence, and an inverted repeat sequence.

Preferably, the plasmid of the present invention comprises, in the replication region, one or more DNA-binding protein binding sequences and two or more repeat motif sequences for at least one sequence selected from the group consisting of a DNA-binding protein binding sequence and a repeat motif sequence.

Preferably, the DNA-binding protein binding sequence is selected from a group consisting of CACCGGTG, ACCGGTG, CCGGTG, ACCGGT, CACAGGT, CACCGGT, CACCGG, GTGCGCAC, GGCCGGCC, TCGGAGCTCCGA (SEQ ID NO: 46), TCCCGGGA, TGCCGGCA, TGATC-GATCA (SEQ ID NO: 47), and GCACGTGC.

Preferably, a repeat unit of the repeat motif sequence is selected from a group consisting of TGGCGTGGTCGTTG (SEQ ID NO: 48), GCGCTGGGGTG (SEQ ID NO: 49), TGGGGCTGTGGTGG (SEQ ID NO: 50), GCGGTGGTG, GCGGTGGTGTG (SEQ ID NO: 51), GGGCCGGGGTTG (SEQ ID NO: 52), GCCGGGGTTGT (SEQ ID NO: 53), TGGTCGTGTTG (SEQ ID NO: 54), TGTTGCTGGGGTG (SEQ ID NO: 55), TGGCGGTGTTGTGG (SEQ ID NO: 56), and GGGGTGCCGGTGG (SEQ ID NO: 57).

Preferably, the plasmid of the present invention comprises one or more oxidant sensitive sequences in the replication region.

Preferably, the oxidant sensitive sequence is selected from a group consisting of TGTGGGGTGGCCCCTCAGC-GAAATA (SEQ ID NO: 58), GGCCTCTCAGC (SEQ ID NO: 59), CTGCGGGCACCTCCTAC (SEQ ID NO: 60), TTCGATGAG, GGTGAGGGGTAACCC (SEQ ID NO: 61), GTGGGGTGGC (SEQ ID NO: 62), GGGGGGTGGCTTC-CTATCG (SEQ ID NO: 63), GTGGGGTGGCCC (SEQ ID NO: 64), TGTGGCGGCGGCACGTGCGCTAA (SEQ ID NO: 65), GCGGGGGCACCCGA (SEQ ID NO: 66), and CTGAGGGTCCTC (SEQ ID NO: 67).

Preferably, the plasmid of the present invention comprises one or more inverted repeat sequences in a replication region.

Preferably, the inverted repeat sequence is selected from a group consisting of GAAAAAGCCGGGCTGCTGCCCG-GCTTTTTC (SEQ ID NO: 68) and CACAGAAAAAGC-CGGGTGGTAGAGCCCGGCTTTTTCCGTG (SEQ ID NO: 69).

Preferably, the base sequence of a replicase-like protein gene is a base sequence of RepA protein gene.

Preferably, the base sequence of a replicase-like protein gene is a base sequence disclosed in SEQ ID NO: 2, or a base sequence that hybridizes under stringent conditions to a base sequence complementary to the base sequence and codes a protein with replicase activity.

Preferably, the base sequence of a DNA-binding protein-like protein gene is a base sequence of a helix-turn-helix protein gene.

Preferably, the base sequence of a DNA-binding protein-like protein gene is a base sequence disclosed in SEQ ID NO: 1, or a base sequence that hybridizes under stringent conditions to a base sequence complementary to the base sequence and codes a helix-turn-helix protein.

Preferably, the replication region is a base sequence disclosed in SEQ ID NO: 3, or a base sequence that hybridizes under stringent conditions to a base sequence complementary to the base sequence.

Preferably, the bacteria are the bacteria of the genus Kocuria.

According to another aspect of the present invention, there is provided a circular plasmid that is autonomously replicable in bacteria of the genus Kocuria, comprising, as for restriction enzyme recognition sites and the number thereof (Restriction enzyme recognition site: Number), SmaI: 2, SphI: 1, SalI: 1, XhoI: 1, and BamHI: 1.

Preferably, the plasmid of the present invention comprises restriction enzyme recognition sites SmaI, SmaI, SphI, SalI, XhoI, BamHI and SacI in that order.

Preferably, in the plasmid of the present invention, the number of base pairs is $3.0 \times 10^3$ to $3.4 \times 10^3$.

Preferably, the plasmid of the present invention is represented by the following restriction enzyme map (I):

[Chemical Formula 1]

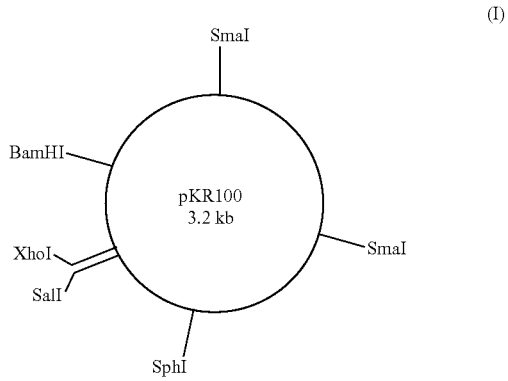

(I)

Preferably, the plasmid of the present invention comprises a base sequence disclosed in SEQ ID NO: 3 or 4.

Preferably, the plasmid of the present invention is derived from Kocuria sp. strain MBE131 (FERN P-21885).

According to another aspect of the present invention, there is provided a DNA fragment comprising a base sequence disclosed in SEQ ID NO: 3, or a base sequence that hybridizes under stringent conditions to a base sequence complementary to the base sequence.

According to another aspect of the present invention, there is provided a vector comprising a base sequence of the DNA fragment of the present invention.

According to another aspect of the present invention, there is provided a transformant comprising the plasmid of the present invention, the DNA fragment of the present invention, or the vector of the present invention.

Advantages of the Invention

According to a plasmid of the present invention, a vector can be constituted to introduce and express a foreign gene in bacteria of the genus Kocuria. Therefore, the use of the plasmid of the present invention makes it possible to introduce useful genes into host cells such as bacteria of the genus Kocuria. Thus, it is possible to add new biological functions to host cells, as well as to improve original functions of host cells.

The use of a DNA fragment and vector of the present invention makes it possible to produce shuttle vectors that are autonomously replicable in bacteria of the genus Kocuria and other bacteria. Among the transformants of the present invention are those created by adding new biological functions to host cells, as well as those created by improving original functions of host cells; the transformants may be used in various fields depending on how the transformants are used.

BRIEF DESCRIPTION OF THE DRAWING

FIG. 2 is a diagram showing a base sequence of pKR100 (SEQ ID NO: 4), clearly indicating regions of base sequences that code ORF1 (SEQ ID NO: 6) and ORF2 (SEQ ID NO: 5), respectively.

FIG. 3 is a diagram showing the base sequence of pKR100 (SEQ ID NO: 4), clearly indicating the regions of base sequences that code ORF1 (SEQ ID NO: 6) and ORF2 (SEQ ID NO: 5), respectively (showing the rest of the base sequence shown in FIG. 2).

FIG. 11A shows the results of aligning a base sequence disclosed in positions 1135-2046 of SEQ ID NO: 3 and a base sequence of Actinosynnema mirum DSM43827 strain (positions 1317895-1318811 of GenBank CP001630.1) (SEQ ID NO: 70).

FIG. 11B shows the results of aligning the base sequence disclosed in positions 1135-2046 of SEQ ID NO: 3 and the base sequence of Actinosynnema mirum DSM43827 strain (showing the rest of the base sequences shown in FIG. 11A) (SEQ ID NO: 70).

FIG. 11C shows the results of aligning the base sequence disclosed in SEQ ID NO: 3 and the base sequence of Actinosynnema mirum DSM43827 strain (showing the rest of the base sequences shown in FIG. 11B) (SEQ ID NO: 70).

MODES FOR CARRYING OUT THE INVENTION

Figure 1:
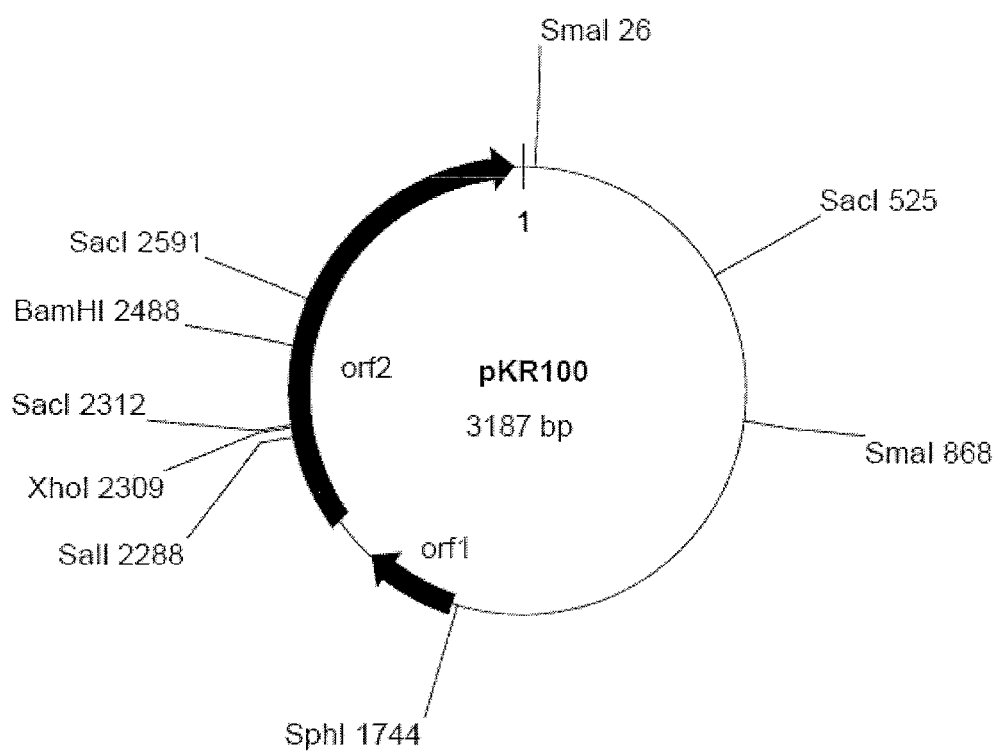
FIG. 1 is a diagram showing a restriction enzyme map of pKR100 to which two open reading frames are added.

Hereinafter, details of the present invention will be described.
[1] Plasmid (1)
First, a circular plasmid that is autonomously replicable in bacteria of the genus *Kocuria* that is one of embodiments of a plasmid of the present invention will be described. Incidentally, the phrase "autonomously replicable" in the present application means that a plasmid exists in cytoplasm of a host cell, and replicates and/or proliferates independently of chromosomal DNA of the host.

Bacteria of the genus *Kocuria* are one type of gram-positive coccus that does not produce hyphae, belonging to the family Micrococcaceae of the suborder Micrococcineae. Bacteria of the genus *Kocuria* are separated from various separation sources, and are isolated for example from mammalian skin, soil, mycorrhizal fungi, fermented food, clinical specimens, fresh water, marine sediment and the like. As for a method of identifying bacteria of the genus *Kocuria*, already-known methods are available without any restriction. For example, the following can be used: genetic-engineering phylogenetic analysis based on 16S rRNA region of a microbial genome, and an identification method based on physiological and biochemical characteristics of microorganisms.

A plasmid of the present invention can be, for example, represented by a restriction enzyme recognition site and the number of restriction enzyme recognition sites. As for a restriction enzyme recognition site and the number of restriction enzyme recognition sites (Restriction enzyme recognition site: Number), one preferred embodiment of a plasmid of the present invention comprises SmaI: 2, SphI: 1, SalI: 1, XhoI: 1, and BamHI: 1. According to the above embodiment, two sites are recognized by restriction enzyme SmaI; one site by SphI; one site by SalI; one site by XhoI; and one site by BamHI.

A more preferred embodiment of a plasmid of the present invention comprises restriction enzyme recognition sites SmaI, SmaI, SphI, SalI, XhoI, and BamHI in that order.

A method of confirming restriction enzyme recognition sites in a plasmid of the present invention is not specifically restricted. For example, the following methods may be employed: a method of confirming restriction enzyme recognition sites by determining a base sequence of a plasmid and then matching restriction enzyme recognition sites; and a method of carrying out restriction enzyme digestion of a plasmid to confirm restriction enzyme recognition sites from a pattern of bands that appear after agarose gel electrophoresis.

It is preferred that the amount of GC contained in a plasmid of the present invention be 60 to 70%. Incidentally, in plasmid pKR100 shown in FIG. 1, which is one of specific embodiments of the present invention described later, the amount of GC contained is about 63%. A method of confirming the amount of GC is not specifically restricted. For example, the following methods may be employed: a method of determining the entire base sequence of a plasmid followed by counting the number of G and C in the base sequence; and a method of hydrolyzing a plasmid into bases followed by counting the number of G and C with the use of chromatography such as HPLC.

A plasmid of the present invention is not specifically restricted as long as the plasmid is autonomously replicable in bacteria of the genus *Kocuria*. Various embodiments are conceivable. As for the overall size thereof, the number of base pairs is about $3.2 \times 10^3$, or more preferably $3.0 \times 10^3$ to $3.4 \times 10^3$. The phrase "about $3.2 \times 10^3$" refers to the number of base pairs in a natural plasmid that is isolated from bacteria of the genus *Kocuria*. The number of base pairs thereof can vary by extracting any region other than a region (also referred to as replication region, hereinafter) that is predicted to have a function of autonomously replicating and/or proliferating in bacteria of the genus *Kocuria*, or by inserting a foreign gene.

A preferred embodiment of a plasmid of the present invention, for example, comprises restriction enzyme recognition sites shown in the following restriction enzyme map (I):

[Chemical Formula 1]

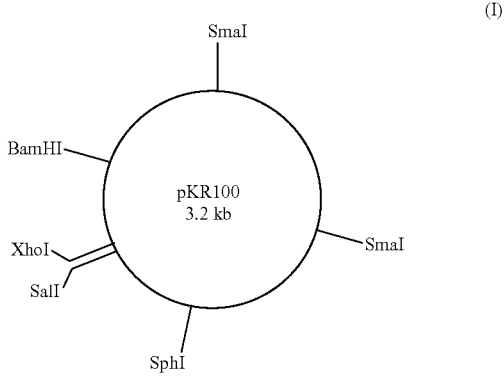

(I)

A more specific embodiment of such a plasmid is plasmid pKR100 shown in FIG. 1.

In FIG. 1, orf1 and orf2 each indicate different open reading frames. A protein (ORF1) coded by orf1 includes 70 amino acids; the molecular weight and the isoelectric point thereof are estimated to be 8.1 kDa and 10.4, respectively. ORF1 is estimated to have two helix structures separated by a random coil structure on the basis of secondary-structure prediction. As a result, ORF1 is estimated to be a DNA-binding protein that forms a helix-turn-helix (HTH) structure, or an analog thereof. In the present application, such a DNA-binding protein that is estimated to form a helix-turn-helix (HTH) structure, and an analog thereof are collectively referred to as a DNA-binding protein-like protein. Furthermore, a base sequence that codes the DNA-binding protein-like protein is referred to as a DNA-binding protein-like protein gene.

A protein (ORF2) coded by orf2 includes 385 amino acids; the molecular weight and the isoelectric point thereof are estimated to be 41 kDa and 11.1, respectively. ORF2 has 31 percent homology (80/257 amino acids, E-value 6e-6) with replication protein RepA (Accession Number YP_345164) derived from *Rhodococcus rhodochrous*. In the present application, such a protein that is estimated to have 30 percent or more homology with RepA and have similar activity to RepA is referred to as a replicase-like protein. A base sequence that codes the replicase-like protein is referred to as a replicase-like protein gene.

The plasmid shown in FIG. 1 comprises orf1, which is a DNA-binding protein-like protein gene, and orf2, which is a replicase-like protein gene. The protein coded by orf2 shows homology with the following: RepA (Accession Number AAA98171; 74/263 amino acid sequences are the same (Similarity 28%)) coded by plasmid pAL5000 that is derived from *Mycobacterium fortuitum*, which is a plasmid having a θ-type replication mode; and RepA (Accession Number BAF45389; 60/210 amino acid sequences are the same (Similarity 28%)) coded by plasmid pNC500 that is derived from *Rhodococcus rhodochrous*, which is a plasmid pertaining to pAL5000. Therefore, the possibility is high that the plasmid of the present invention would be θ (theta)-type, which replicates in a stable manner. Accordingly, the plasmid of the present invention is preferably a plasmid of a θ-type replication mode.

The base sequence of the plasmid shown in FIG. 1 is not specifically restricted as long as the base sequence comprises the restriction enzyme recognition site, DNA-binding protein-like protein gene, and replicase-like protein gene shown in FIG. 1. However, it is preferred that the base sequence of the plasmid comprises a base sequence shown in FIGS. 2 and 3 (SEQ ID NO: 4).

A base sequence shown in FIG. 2 comprises H-site-like seq in an upstream region of orf1 (a sequence indicated by lower-case letters in FIG. 2). H-site-like seq indicates a sequence that shows homology with a sequence called GCbox, which is comprised in High affinity site (H-site) that is known as a replication protein binding site that exists in a replication initiation region of plasmid pAL5000 derived from *Mycobacterium fortuitum* (See "Stolt P, Stoker N G., Nucleic Acids Res. 1997, 25 (19): 3840-6"; the disclosures of the document are incorporated herein by reference). Moreover, H-site in pAL5000 is characterized by a structure that comprises a 100%-matching palindrome consisting of eight bases that is called GCbox. Therefore, in the present application, a sequence having a 100%-matching palindrome structure consisting of eight or more bases is also referred to as H-site-like seq. Furthermore, in the present application, as in the case of H-site-like seq, a sequence that binds to a DNA-binding protein such as a replication protein is referred to as a DNA-binding protein binding sequence.

The base sequence shown in FIG. 2 comprises an oxidant sensitive sequence in an upstream region of orf1 (a sequence indicated by italic with dotted line in an upper portion of FIG. 2). In general, it is known that, when RepB protein, which is a DNA-binding protein, binds to H-site on DNA, the DNA bends (See "Chatterjee S, Basu A, Basu A, Das Gupta S K., J. Bacteriol. 2007, 189 (23): 8584-92."; the disclosures of the document are incorporated herein by reference). Around a bent portion of the DNA, there is a region of a base sequence that shows sensitivity to an oxidant (referred to as an oxidant sensitive sequence). Given that the oxidant sensitive sequence shows sensitivity to an oxidant, it is estimated that the dissociation of the DNA arises in the above sequence, suggesting that replication is initiated from the oxidant sensitive sequence. As for the oxidant sensitive sequence and a nearby base sequence, the following sequence and a complementary strand thereof are known: TGTGGGGTGGCCCCT-CAGCGAAATA (SEQ ID NO: 58). The base sequence shown in FIG. 2 comprises, as shown in the diagram, a sequence that has homology with SEQ ID NO: 58 and a complementary strand thereof as an oxidant sensitive sequence.

The base sequence shown in FIG. 2 comprises an approximate repeat motif sequence (direct repeat sequence) in an upstream region of orf1 (a sequence indicated by bold letters with solid line in a lower portion of FIG. 2). Moreover, the base sequence shown in FIG. 2 comprises approximate inverted repeat sequences in an upstream region of orf1 and between orf1 and orf2 (a sequence indicated by arrow in a lower portion of FIG. 2). In general, it is known that, during the replication and copy number control of a θ (theta)-type plasmid family, iteron, which is a repeat motif sequence, plays an important role as cis-element (See "Chattoraj D K., Mol. Microbiol. 2000, 37 (3): 467-76." and "Cha K I, Lim K, Jang S, Lim W, Kim T, Chang H., J Microbiol Biotechnol. 2007, 17 (11): 1841-7."; the disclosures of the documents are incorporated herein by reference). A cis-element means an element that plays a role in controlling a gene that the cis-element holds, and is distinguished from an element (trans-element) that can be supplied from the outside such as genomes and other plasmids. For example, as for pCD3.4, which is a θ-type plasmid, there is a report that the copy number thereof decreases due to removal of one iteron, resulting in a decrease in the stability of the plasmid (See "van Belkum M J, Stiles M E., Microbiology. 2006, 152: 171-8.";

the disclosures of the document are incorporated herein by reference). As for p705/5, which is a θ-type plasmid, there are reports that, as RepA protein binds to an inverted repeat sequence that exists in a promoter region of repA gene, transcription of RepA protein is suppressed, and the copy number of the plasmid is regulated (See the above documents by Cha K I et al.). Meanwhile, there are also reports that there is a θ-type plasmid from which an inverted repeat sequence cannot be discovered (See the above documents by van Belkum M J et al.).

For example, it is predicted that in pAL5000, repeat motif sequence (iteron), repA gene, and repB gene may be sequences that play a role in autonomous replication of pAL5000. There is a report that, if a plasmid that has neither repA gene nor repB gene derived from pAL5000 but has a repeat motif sequence derived from pAL5000 is supplied in trans with RepA and RepB proteins derived from other plasmids, then the plasmid that has the repeat motif sequence derived from pAL5000 becomes replicable (See "Stolt P, Stoker N G., Microbiology. 1996, 142 (Pt 10): 2795-802."; the disclosures of the document are incorporated herein by reference). As reported in the document, it is estimated that the repeat motif sequence is a cis-element that is involved in the incompatibility, copy number, and stability of plasmid.

As described in Example 8, the present inventors prepared plasmid pKR141 that has a region of the $1,031^{st}$ to $3,170^{th}$ of the base sequence (SEQ ID NO: 3), comprising one set of a plurality of repeat motif sequences and one inverted repeat sequence, in the base sequence shown in FIG. 2. Then, the present inventors found that pKR141 is autonomously replicable in bacteria of the genus Kocuria. Therefore, as for any region other than the $1,031^{st}$ to $3,170^{th}$ of the base sequence shown in FIG. 2, it is possible to insert a foreign gene, or to replace with a foreign gene.

The base sequence disclosed in SEQ ID NO: 3 is a unique base sequence. For example, when a homology search is performed as to the base sequence disclosed in SEQ ID NO: 3 by the FASTA search at DDBJ, what appears at the top is Actinosynnema mirum DSM43827 strain, which has about 54-percent sequence similarity (http://fasta.ddbj.nig.ac.jp/top-j.html; Regarding the FASTA search, see "Pearson W R, Lipman D J., (1998), Proc Natl Acad Sci USA. 85 (8): 2444-8, Lipman D J, Pearson W R., (1985), Science. 227 (4693): 1435-41," and "Wilbur W J, Lipman D J., (1983), Proc Natl Acad Sci USA. 80(3): 726-30"; the disclosures of the documents are incorporated herein by reference). The results of alignment between the base sequence disclosed in SEQ ID NO: 3 and the base sequence of Actinosynnema mirum DSM43827 strain are shown in FIG. 11.

The base sequence disclosed in SEQ ID NO: 3 is a unique base sequence. Therefore, the possibility is high that the following plasmid autonomously replicates in bacteria of the genus Kocuria: a plasmid that is derived from bacteria of the genus Kocuria, is in the form of being linearly single-stranded, and hybridizes under stringent conditions to a DNA fragment comprising a base sequence complementary to a base sequence consisting of successive 500 or more bases out of the base sequence disclosed in SEQ ID NO: 3, or preferably 1,000 or more bases, or more preferably 1,500 or more bases, or still more preferably 1,700 or more bases, or even more preferably 1,900 or more bases. Accordingly, such a plasmid is also among the plasmids of the present invention.

The phrase "hybridize under stringent conditions" in the present application means a DNA base sequence obtained by colony hybridization method, plaque hybridization method, Southern blot hybridization method, or any other method with the use of DNA as a probe. For example, the DNA identified by the following procedure and other DNAs can be included: with the use of a filter to which a DNA derived from a colony or plaque, or a fragment of the DNA, has been fixed, in the presence of 0.5 to 2.0M NaCl, hybridization is carried out at 40 to 75 degrees Celsius; preferably in the presence of 0.7 to 1.0M NaCl, hybridization is carried out at 65 degrees Celsius; then, with the use of 0.1 to 2×SSC solution (1×SSC solution is prepared from 150 mM of sodium chloride and 15 mM of sodium citrate), the filter is cleaned under a 65-degree-Celsius condition. The preparation of the probe and hybridization may be performed in a way that complies with the methods disclosed in the following documents or other documents (the disclosures of the documents are incorporated herein by reference): "Molecular Cloning: A laboratory Manual, 2nd ED., Cold Spring Harbor Laboratory, Cold Spring Harbor, N.Y., 1989 (simply referred to as "Molecular Cloning 2nd Edition," hereinafter)"; "Current Protocols in Molecular Biology, Supplement 1 to 38, John Wiley & Sons (1987-1997) (simply referred to as "Current Protocols in Molecular Biology," hereinafter)." Incidentally, a person of ordinary skill in the art can set a condition for acquiring a replication region in a plasmid of the present invention by taking into consideration various factors including factors such as the salt concentration and temperature of such a buffer as well as other factors, such as the concentration of the probe, the length of the probe, and reaction time.

As for the DNA fragment containing a base sequence that hybridizes under stringent conditions, the following DNA can be included: a DNA having a predetermined level of homology (similarity) with a base sequence of a DNA that is used as a probe. For example, what can be included is a DNA fragment that has 70% or more homology, or preferably 80% or more homology, or more preferably 90% or more homology, or still more preferably 93% or more homology, or particularly preferably 95% or more homology, or most preferably 98% or more homology.

The base sequences that hybridize under stringent conditions to a base sequence complementary to the base sequence disclosed in SEQ ID NO: 3, for example, include a base sequence that is obtained as the deletion, replacement, and/or addition of one or more bases is performed on the base sequence disclosed in SEQ ID NO: 3: the number of bases deleted, replaced and/or added is one to several, preferably 1 to 50, or more preferably 1 to 30, or still more preferably 1 to 20, or even more preferably 1, 2, 3, 4, 5, 6, 7, 8, 9, or 10.

The phrase "deletion of a base" means that a base in a sequence is lost or deleted. The phrase "replacement of a base" means that a base in a sequence is replaced with another base. The phrase "addition of a base" means that a base is added.

According to a method disclosed in examples, it is possible to confirm whether or not a plasmid comprising a base sequence that hybridizes under stringent conditions to a base sequence complementary to the base sequence disclosed in SEQ ID NO: 3 is autonomously replicable in bacteria of the genus Kocuria. The method, when briefly described, includes the processes of: preparing a recombinant plasmid, which is constituted by connecting a drug resistance gene to a base sequence that hybridizes under stringent conditions to a base sequence complementary to the base sequence disclosed in SEQ ID NO: 3; producing a transformant by introducing the recombinant plasmid into bacteria of the genus Kocuria; culturing the transformant in the presence of a drug associated with the drug resistance gene; and then confirming proliferation of the transformant.

A plasmid having a base sequence shown in FIGS. 2 and 3 (SEQ ID NO: 4) can be isolated from Kocuria sp. strain MBE131 (FERN P-21885) (which may be simply referred to as strain MBE131, hereinafter). However, a plasmid of the present invention may be a plasmid that is isolated from the strain MBE 131, does not always comprise all of the base sequence disclosed in SEQ ID NO: 4, and comprises at least the base sequence disclosed in SEQ ID NO: 3.

A method of extracting the plasmid from bacteria of the genus *Kocuria* is not specifically restricted. For example, the following method can be included: a method of using a suitable culture medium such as YTNM medium and proliferating bacteria of the genus *Kocuria* under conditions suitable for proliferation of the bacteria of the genus *Kocuria*, i.e. at 15 to 30 degrees Celsius for one to three days by means of static culture or shaking culture for example; recovering bacterial cells by performing centrifugal separation or other operations; dissolving cell walls of the bacterial cells by performing lysozyme treatment and other operations; and then recovering plasmids with the use of a plasmid extraction kit such as High pure plasmid purification kit (manufactured by Roche).

A method of confirming whether or not a plasmid extracted from bacteria of the genus *Kocuria* comprises the base sequence disclosed in SEQ ID NO: 3 or 4 is not specifically restricted. For example, the following and other methods can be included: a hybridization method that uses a DNA or RNA probe prepared based on information regarding the base sequence disclosed in SEQ ID NO: 3 or 4; a method of performing restriction enzyme digestion on the basis of a restriction enzyme map of pKR100 followed by confirming the size of a DNA that appears after the digestion through agarose gel electrophoresis.

As for another method of acquiring a plasmid of the present invention, for example, the plasmid can be isolated from among the plasmids extracted from the strain MBE 131 or other bacteria of the genus *Kocuria* by using a probe or a PCR primer set synthesized on the basis of information regarding the base sequence disclosed in SEQ ID NO: 3 or 4 so as to be able to hybridize to the base sequence.

The plasmids of the present invention are connected to a foreign gene, and are then introduced into host cells such as bacteria of the genus *Kocuria* by an already-known DNA introduction method such as an electroporation method, a protoplast method, or a method with the use of calcium ions. Therefore, the plasmids of the present invention are available to prepare a transformant that expresses a foreign gene.

When being connected to a DNA replication region of a plasmid that is autonomously replicable in host cells different from bacteria of the genus *Kocuria*, the plasmids of the present invention are available to constitute a shuttle vector that is autonomously replicable in bacteria of the genus *Kocuria* and in host cells different from the bacteria of the genus *Kocuria*. A method of constituting a shuttle vector with the use of a plasmid of the present invention is not specifically restricted. For example, it is possible to constitute a shuttle vector whose host cells are bacteria of the genus *Kocuria* and *Escherichia coli* by connecting all of the plasmid of the present invention, or part thereof that comprises a region playing a role in DNA replication, to a multicloning site of a plasmid that is autonomously replicable in *Escherichia coli* such as pHY300PLK.

[2] Plasmid (2)

According to another embodiment of the present invention, a circular plasmid can be included that has one of replication regions of the following (A) to (C), which is estimated to have a function of autonomously replicating in bacteria, or preferably bacteria of the genus *Kocuria* or other bacteria of the family Micrococcaceae:

(A) A replication region that comprises a base sequence of a DNA-binding protein-like protein gene; a base sequence of a replicase-like protein gene; and a base sequence disclosed in SEQ ID NO: 45, or a base sequence that hybridizes under stringent conditions to a base sequence complementary to the base sequence, (B) A replication region that comprises a base sequence of a DNA-binding protein-like protein gene; a base sequence of a replicase-like protein gene; and at least one sequence selected from a group consisting of a DNA-binding protein binding sequence and a repeat motif sequence, (C) A replication region that comprises a base sequence of a DNA-binding protein-like protein gene; a base sequence of a replicase-like protein gene; and a base sequence comprising at least one sequence selected from a group consisting of a DNA-binding protein binding sequence and a repeat motif sequence, an oxidant sensitive sequence, and an inverted repeat sequence.

DNA-binding proteins are proteins that have a structure able to bind to DNA, and are classified in terms of structure into the following and other groups: homeodomain, Zinc finger domain, winged helix, Leucine zipper protein, helix-loop-helix (HLH) protein, and helix-turn-helix (HTH) protein. As for a base sequence of a DNA-binding protein-like protein gene in the replication regions (A) to (C) of a plasmid of the present invention, for example, base sequences of the gene of the DNA-binding protein can be included without limitation. However, the base sequence is preferably a base sequence of helix-turn-helix protein gene, or more preferably the base sequence disclosed in SEQ ID NO: 1 or a base sequence that hybridizes under stringent conditions to a base sequence complementary to the base sequence and codes a helix-turn-helix protein.

A replicase-like protein is a protein having replicase activity to dissociate the double helix or secondary structure of nucleic acid along a phosphoric acid ester skeleton of nucleic acid, and may be structured in various ways. As for the functions of a replication protein (or replicase), there is the following document: "Hiraga S, Sugiyama T, Itoh T., J. Bacteriol. 1994 December; 176(23): 7233-43" (the disclosures of the document are incorporated herein by reference). For example, the document states that "The Rep protein specifically binds to the origin and synthesizes a unique primer RNA at the origin."

As for a base sequence of a replicase-like protein gene in the replication regions (A) to (C) of a plasmid of the present invention, for example, a base sequence of the gene of RepA protein can be included. Preferably, the base sequence is the base sequence disclosed in SEQ ID NO: 2 or a base sequence that hybridizes under stringent conditions to a base sequence complementary to the base sequence and codes a protein having replicase activity.

The replication region (A) of a plasmid of the present invention comprises a base sequence disclosed in SEQ ID NO: 45 or a base sequence that hybridizes under stringent conditions to a base sequence complementary to the base sequence, as well as a base sequence of DNA-binding protein gene and a base sequence of replicase-like protein gene. The base sequence disclosed in SEQ ID NO: 45 or the base sequence that hybridizes under stringent conditions to a base sequence complementary to the base sequence comprises the following and other sequences, which are regions that are estimated to be involved in autonomous replication in bacteria of the genus *Kocuria* of a plasmid of the present invention: a DNA-binding protein binding sequence, a repeat motif sequence, an oxidant sensitive sequence, and an inverted repeat sequence. The base sequence that hybridizes under stringent conditions to a base sequence complementary to the base sequence disclosed in SEQ ID NO: 45 preferably comprises at least one sequence selected as a DNA-binding protein binding sequence from a group consisting of TGCCG-GCA, TGATCGATCA (SEQ ID NO: 47), GCACGTGC, and CACCGGT; at least one type of sequence selected as a repeat motif sequence from a group consisting of GGGC-CGGGGTTG (SEQ ID NO: 52), TGGTCGTGTTG (SEQ ID NO: 54), TGTTGCTGGGGTG (SEQ ID NO: 55), TGGCG-GTGTTGTGG (SEQ ID NO: 56), and GGGGTGCCG-GTGG (SEQ ID NO: 57); at least one type of sequence selected as an oxidant sensitive sequence from a group consisting of GGGGGGTGGCTTCCTATCG (SEQ ID NO: 63), GTGGGGTGGCCC (SEQ ID NO: 64), TGTGGCGGCG-GCACGTGCGCTAA (SEQ ID NO: 65), GCGGGGGCAC-CCGA (SEQ ID NO: 66), and CTGAGGGTCCTC (SEQ ID NO: 67); and, as an inverted repeat sequence, GAAAAAGC-CGGGCTGCTGCCCGGCTTTTTC (SEQ ID NO: 68) or CACAGAAAAAGCCGGGTGGTAGAGCCCG-GCTTTTTCCGTG (SEQ ID NO: 69).

Examples of a DNA-binding protein binding sequence in the replication regions (B) and (C) of a plasmid of the present invention can include CACCGGTG, ACCGGTG, CCGGTG, ACCGGT, CACAGGT, CACCGGT, CACCGG, GTGCG-CAC, GGCCGGCC, TCGGAGCTCCGA (SEQ ID NO: 46), TCCCGGGA, TGCCGGCA, TGATCGATCA (SEQ ID NO: 47), and GCACGTGC.

Examples of a repeat unit of a repeat motif sequence in the replication regions (B) and (C) of a plasmid of the present invention can include TGGCGTGGTCGTTG (SEQ ID NO: 48), GCGCTGGGGTG (SEQ ID NO: 49), TGGGGCTGTG-GTGG (SEQ ID NO: 50), GCGGTGGTG, GCGGTGGT-GTG (SEQ ID NO: 51), GGGCCGGGGTTG (SEQ ID NO: 52), GCCGGGGTTGT (SEQ ID NO: 53), TGGTCGTGTTG (SEQ ID NO: 54), TGTTGCTGGGGTG (SEQ ID NO: 55), TGGGGCTGTGGTGG (SEQ ID NO: 56), and GGGGTGC-CGGTGG (SEQ ID NO: 57).

Examples of an oxidant sensitive sequence in the replication region (C) of a plasmid of the present invention can include TGTGGGGTGGCCCCTCAGCGAAATA (SEQ ID NO: 58), GGCCTCTCAGC (SEQ ID NO: 59), CTGCGGGCACCTCCTAC (SEQ ID NO: 60), TTCGAT-GAG, GGTGAGGGGTAACCC (SEQ ID NO: 61), GTGGGGTGGC (SEQ ID NO: 62), GGGGGGTGGCTTC-CTATCG (SEQ ID NO: 63), GTGGGGTGGCCC (SEQ ID NO: 64), TGTGGCGGCGGCACGTGCGCTAA (SEQ ID NO: 65), GCGGGGGCACCCGA (SEQ ID NO: 66), and CTGAGGGTCCTC (SEQ ID NO: 67).

Examples of an inverted repeat sequence in the replication region (C) of a plasmid of the present invention can include GAAAAAGCCGGGCTGCTGCCCGGCTTTTTC (SEQ ID NO: 68) and CACAGAAAAAGCCGGGTGGTAGAGC-CCGGCTTTTTCCGTG (SEQ ID NO: 69).

As described below in Example 2, a region that comprises either the DNA-binding protein binding sequence or the repeat motif sequence, or both of them, is estimated to be involved in the replication and stable retention of a plasmid in the replication region. Accordingly, the replication regions (B) and (C) of a plasmid of the present invention comprises the DNA-binding protein binding sequence, the repeat motif sequence or DNA-binding protein binding sequence, and the repeat motif sequence. Moreover, the replication regions (B) and (C) of a plasmid of the present invention may comprise either two or more DNA-binding protein binding sequences or two or more repeat motif sequences, or comprise both two or more DNA-binding protein binding sequences and two or more repeat motif sequences.

The replication region (C) of a plasmid of the present invention comprises an oxidant sensitive sequence and an inverted repeat sequence. As described above, the oxidant sensitive sequence is a sequence that is estimated to be involved in the initiation of replication; and the inverted repeat sequence is a sequence to which a replicase-like protein binds and which is able to control the copy number of a plasmid as a result. The replication region (C) of a plasmid of the present invention comprises the above sequences, it is possible to control autonomous replication of the plasmid. Incidentally, it is preferred that an inverted repeat sequence be comprised in the replication regions (A) and (B) of a plasmid of the present invention.

The number of sequences of each type in the replication regions (A) to (C) of a plasmid of the present invention, as well as the order the sequences are arranged, is not specifically restricted as long as the plasmid of the present invention is autonomously replicable in bacteria; and thus various embodiments are possible.

One embodiment of the replication regions (A) to (C) in a plasmid of the present invention is the base sequence disclosed in SEQ ID NO: 3 or a base sequence that hybridizes under stringent conditions to a base sequence complementary to the base sequence.

[3] DNA Fragment, Vector, and Transformant

According to another aspect of the present invention, there is provided a DNA fragment having the base sequence disclosed in SEQ ID NO: 3 or a base sequence that hybridizes under stringent conditions to a base sequence complementary to the base sequence. By introducing those obtained by connecting the DNA fragment of the present invention to a foreign gene into chromosomes of host cells such as bacteria of the genus *Kocuria* or into cytoplasm of host cells as cyclized plasmids, it is possible to obtain a transformant that expresses the foreign gene.

The DNA fragment of the present invention can be synthesized by the above PCR or any other already-known. DNA synthesis method without restriction. Examples of DNA synthesis can include (the disclosures of the following documents are incorporated herein by reference): a method of chemically synthesizing the DNA fragment on the basis of information regarding the base sequence disclosed in SEQ ID NO: 3 by means of a phosphotriester method, a phosphoamidite method, or the like [J. Am. Chem. Soc., 89, 4801 (1967); J. Am. Chem. Soc., 91, 3350 (1969); Science, 150, 178 (1968); Tetrahedron Lett., 22, 1859 (1981); Tetrahedron Lett., 24, 245 (1983)]; genetic-engineering methods, such as a method of introducing site-specific mutation into the base sequence disclosed in SEQ ID NO: 3 [Methods in Enzymology, 154, 350, 367-382 (1987); Methods in Enzymology, 100, 468 (1983); Nucleic Acids Res., 12, 9441 (1984); Sequel of Biochemical Experiment Course 1 "Genetic Research Method II," Japanese Biochemical Society, p105 (1986)]; and a combination of the methods described above. For example, the DNA synthesis may be achieved by chemosynthesis due to a phosphoramidite method or a triester method. Moreover, a commercially-available automated oligonucleotide synthesis device may also be used.

The DNA fragment of the present invention may be inserted into an already-known vector and then introduced into a target cell corresponding to the vector. For example, such a vector may be one which is autonomously replicable, or one which is integrated into the chromosome of a target cell when being introduced into the target cell followed by being replicated together with the chromosome. A preferred example of the vector is an expression vector. Examples of the expression vector can include plasmid vector, phage vector, virus vector, and the like. The DNA fragment of the present invention is functionally linked along with an element (e.g. promoter or the like) required for transcription in an expression vector. The promoter is a DNA sequence that shows transcriptional activity in a target cell, and can be appropriately selected according to the type of the target cell.

A vector comprising the DNA fragment of the present invention is among other embodiments of the present invention. A preferred embodiment of a vector of the present invention is a plasmid of the present invention. A transformant comprising a plasmid or vector of the present invention is also among other embodiments of the present invention.

In the present application, the preparation of primers and probes, extraction of plasmid DNA, ligation, introduction of DNA, cloning, and other operations are already known to a person of ordinary skill in the art. For example, the above operations can be carried out in a way that complies with the methods described in Molecular Cloning 2nd Edition, Current Protocols in Molecular Biology, and the like.

The following describes the present invention in more detail through examples. However, the present invention is not limited to the examples.

EXAMPLES

Example 1

Isolation of Plasmid Derived from *Kocuria* Bacteria

About 250 strains of bacteria of the suborder Actinomyces were isolated from the bottom sediment at a depth of about 2,000 meters in Sagami Bay. Among the strains, it was confirmed as described in the following that *Kocuria* sp. strain MBE131, which was a bacterium of the genus *Kocuria*, retained plasmid DNA. Strain MBE131 was cultured in YTNM medium (1.6% of bacto-tryptone, 0.5% of yeast extract, 1% of sodium chloride, and 0.1% of magnesium sulfate) at 25 degrees Celsius for two days by means of shaking culture. Bacterial cells were obtained by centrifugation from the culture. The bacterial cells were incubated in a 20 mM Tris-HCl buffer containing lysozyme (2 mg/mL) at 37 degrees Celsius for one hour so that cell walls of the bacterial cells were lysed. The plasmid DNA was then prepared from the lysate using High pure plasmid purification kit (manufactured by Roche).

Example 2

Sequencing Analysis of Plasmid pKR100

The fragments that were obtained by digesting the plasmid prepared in Example 1 with restriction enzyme BamHI or SalI were each cloned to plasmid vector pUC18, and the entire base sequence of each was determined. As a result, it was found that the clones were circular plasmids that had an insert fragment made up of completely identical base sequence, respectively. The plasmid was named pKR100. The base sequence thereof is disclosed in SEQ ID NO: 4 and shown in FIG. 1. FIG. 1 shows a restriction enzyme map of the plasmid, in which ORF is also shown. The base sequence of plasmid pKR100 was analyzed using GENETYX MAC program Ver. 12.1.1 (manufactured by GENETYX CORPORATION). The base length of plasmid pKR100 was 3,187; the amount of G+C contained was 63%.

Among the region represented by the $1^{st}$ to $1,751^{st}$ of SEQ ID NO: 1, a plurality of the following structures were detected (See FIG. 1): the direct repeat structure made up of approximate repeat motif sequences (indicated by bold letters with solid line under the base sequence in FIG. 2), and the inverted repeat (hairpin structure) (indicated by arrow under the base sequence in FIG. 2). Therefore, it was suggested that the above region is a region that was involved in the replication of plasmid and the regulation of copy number. Moreover, across the entire length of pKR100, a search for the direct repeat (repeat motif sequence) was performed by GENETYX-MAC. As a result, the following sequence was detected: a 100%-matching repeat sequence that includes 14 base pairs (TGGGGCTGTGGTGG (SEQ ID NO: 50)) at the $742^{nd}$ to $755^{th}$ bases and the $756^{th}$ to $769^{th}$ bases. Then, with the use of the repeat motif sequence including the 14 base pairs (TGGGGCTGTGGTGG (SEQ ID NO: 50)), a region having homology with the repeat motif sequence was searched for. At the $1,278^{th}$ to $1,291^{st}$ bases, TGGCGGTGTTGTGG (SEQ ID NO: 56) was discovered and consistent with the $742^{nd}$ to $755^{th}$ bases in the ratio of 11/14 bases. Moreover, at the $410^{th}$ to $420^{th}$, $876^{th}$ to $884^{th}$, $1,000^{th}$ to $1,011^{th}$, $1,170^{th}$ to $1,182^{nd}$, and $1,723^{rd}$ to $1,735^{th}$ bases, there were sites that showed homology. Similarly, the $1,278^{th}$ to $1,291^{st}$ bases (TGGCGGTGTTGTGG (SEQ ID NO: 56), which showed homology with the repeat motif sequence (TGGGGCTGTGGTGG (SEQ ID NO: 50), the $742^{nd}$ to $755^{th}$ and $756^{th}$ to $769^{th}$ bases), was searched for a region that showed homology therewith. As a result, the following bases showed homology: the $742^{nd}$ to $755^{th}$, $376^{th}$ to $389^{th}$, $876^{th}$ to $886^{th}$, $1,002^{nd}$ to $1,012^{th}$, and $1,164^{th}$ to $1,174^{th}$ bases. Therefore, it was suggested that any one of the approximate repeat sequences of pKR100 was involved in the replication of pKR100 and the regulation of the copy number.

Across the entire length of pKR100, a search for the inverted repeat & complementary sequences was carried out by GENETYX. As a result, the inverted repeat sequences were detected at the $806^{th}$ to $835^{th}$ and $1,322^{nd}$ to $1,361^{st}$ bases.

In pKR100, among the region represented by the $1^{st}$ to $1,751^{st}$, the following sequence (indicated by lower-case letters in FIG. 1) was detected: a sequence that had homology with a sequence called GCbox in High affinity site (H-site), which was known as a replication protein binding site that existed in a replication initiation region of plasmid pAL5000 derived from *Mycobacterium fortuitum*. Moreover, across the entire length of pKR100, a homology search was performed by gene analysis software GENETYX-MAC ver. 12.1.0 (manufactured by GENETYX CORPORATION) with the use of the sequence CACCGGTG, which was called GCbox consisting of the most important 8 base pairs out of H-site (DNA-binding protein binding sequence). As a result, a portion in which the successive seven bases were completely consistent with the GCbox was detected in the base sequence of the $442^{nd}$ to $448^{th}$ of pKR100 and in the base sequence of the $1,399^{th}$ to $1,405^{th}$. Therefore, it was predicted that the above portions of H-site-like seq would be a base sequence that took an important role in binding of RepB protein to plasmids. Thus, it was assumed that one of the H-site-like seq portions, or both of them, would be involved in the replication of pKR100.

As for the oxidant sensitive sequence that was estimated to be involved in the initiation of replication, a homology search with the use of TGTGGGGTGGCCCCTCAGCGAAATA (SEQ ID NO: 58) was performed for the overall length of pKR100 by means of GENETYX-MAC. As a result, a site that showed homology with the above sequence was detected in a non-orf region of pKR100. It was estimated that it was highly possible that one out of the sequence portions showing homology with TGTGGGGTGGCCCCTCAGCGAAATA (SEQ ID NO: 58) would function as a replication origin of pKR100. In particular, as for TGTGGGG, high levels of homology were found in the $1,200^{th}$ to $1,211^{th}$ bases (GTGGGGTGGCCC (SEQ ID NO: 64)) and in the 370$^{th}$ to 379$^{th}$ bases (GTGGGGTGGC (SEQ ID NO: 62)). Moreover, a plurality of other sequences showing homology were also detected. It was estimated that it was highly possible that one or a plurality of the above sequences would be involved in the initiation of replication as dissociation points of DNA.

As described above, it was estimated that, among the non-orf regions of pKR100, a region comprising either the direct repeat made up of approximate repeat motif sequences or the H-site-like sequence, or both of them, had a function related to the replication and stable retention of plasmids.

Then, an analysis of open reading frame was performed, and the results suggested that two open reading frames (orf1 and orf2) could exist (See FIG. 1). The protein (ORF1) coded by orf1 included 70 amino acids; the molecular weight thereof was estimated to be 8.1 kDa, and the isoelectric point thereof 10.4 as a result of calculation. A homology search for the amino acid sequence coded by orf1 was performed using the BLAST program by the National Center for Biotechnology Information (NCBI). However, no amino acid sequence to match ORF1 was found on the database.

With the use of the amino acid sequence of ORF1, a secondary-structure prediction was performed by APSSP2: Advanced Protein Secondary Structure Prediction Server (http://www.imtech.res.in/raghava/apssp2/) (See "Raghava, G. P. S. (2002) APSSP2: A combination method for protein secondary structure prediction based on neural network and example based learning. CASP5. A-132."; the disclosures of the document are incorporated herein by reference). As a result, it was predicted that ORF1 had two helix structures separated by a random coil structure. It is suggested that ORF1 would be a DNA-binding protein forming a unique helix-turn-helix (HTH) structure that could be typically found in a DNA-binding protein. The protein (ORF2) coded by orf2 included 385 amino acids; the molecular weight thereof was estimated to be 41 kDa, and the isoelectric point thereof 11.1 as a result of calculation. A search for a protein matching ORF2 was conducted by the BLAST program provided by NCBI. As a result, ORF2 was found to have homology with a replicase superfamily protein. However, as for those with highest levels of homology, only replication proteins (Accession Number YP__345164) derived from *Rhodococcus rhodochrous* were found to be only 31% (80/257 amino acids, E-value 6e-6) identical. It was suggested that ORF2 was a protein involved in the replication of plasmid pKR100.

Example 3

Phylogenetic Analysis of Strain MBE131

From the entire DNA of the strain MBE 131 obtained in Example 1, the 16S rRNA gene was amplified with the use of primer sets made up of the base sequences disclosed in SEQ ID NO:s 7 and 8. An amplified fragment was purified using Wizard PCR purification kit (manufactured by Promega KK.), and the base sequence thereof was determined. The 16S rRNA gene sequence of the strain MBE 131 showed 99% base sequence similarity to the 16S rRNA gene sequence (Accession Number X87756) of a standard strain of *Kocuria rosea* registered in the database. Therefore, in terms of phylogenetic systematics, the strain MBE 131 was assumed to be the most closely-related species to *Kocuria rosea*.

Example 4

Figure 5:
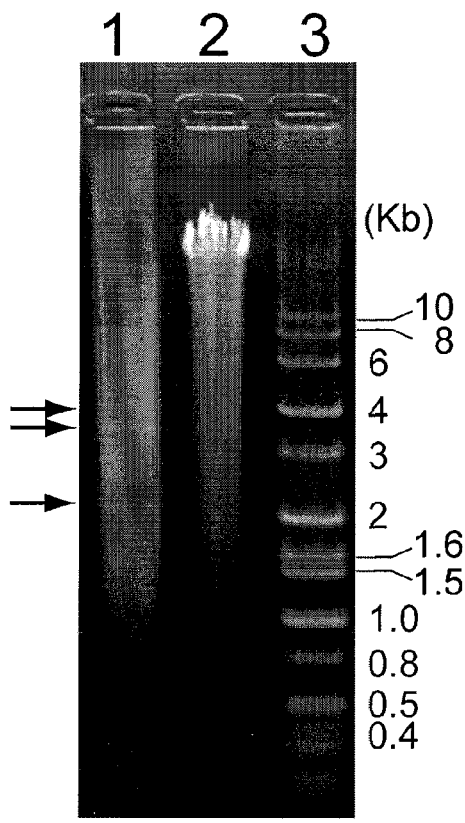
FIG. 5 is a diagram showing the results of detecting plasmids through DNA extraction from *Kocuria* sp. strain MBE131 and *Kocuria rosea* standard strain in Example 3. Lane 1 shows a DNA extracted from the strain MBE 131. Lane 2 shows a DNA extracted from the *Kocuria rosea* standard strain. Lane 3 shows a DNA size marker.

Comparison Between *Kocuria* sp. Strain MBE131 and *Kocuria rosea* Standard Strain The strain MBE 131 was cultured for two days in YTMN medium at 25 degrees Celsius. In a similar way to Example 1, from the bacterial cells obtained, an extraction operation of plasmids was conducted with the use of a plasmid purification kit. Meanwhile, the standard strain of *Kocuria rosea* (NBRC15588), which was a bacterium of the genus *Kocuria* reserved by a bacterial-cell preservation organization, was cultured under the same conditions, and the same operation was conducted on the bacterial cells obtained from the culture. Then, each of the DNA solutions extracted from the above two strains was loaded into agarose gel electrophoresis (See FIG. 5). As a result, the band of plasmid DNA was detected in the case of the strain MBE 131. However, the band was not detected in the case of the standard strain of *Kocuria rosea*.

Furthermore, with each of the extracted DNA solutions as a template, the PCR was carried out with the use of primer sets A to F (Table 1) of forward and reverse primers that had a sequence complementary to the base sequence of pKR100.

TABLE 1

| Set No. | Forward primer | Reverse primer |
|---|---|---|
| A | TGGTGGCGGTGTTGTG | TCGCGAACGAAGTTCAGG |
| B | GCCGGTGGCAAGGAGAGCATGCACAT GGGCGACCCTC | CACTGGCCTACTGACGGACC |
| C | GGTCCGTCAGTAGGCCAGTG | GGAGACTGTTTCAGAG |
| D | TGGTGGCGGTGTTGTG | CACTGGCCTACTGACGGACC |
| E | GCCGGTGGCAAGGAGAGCATGCACAT GGGCGACCCTC | GGAGACTGTTTCAGAG |
| F | TGGTGGCGGTGTTGTG | GGAGACTGTTTCAGAG |

Figure 6:
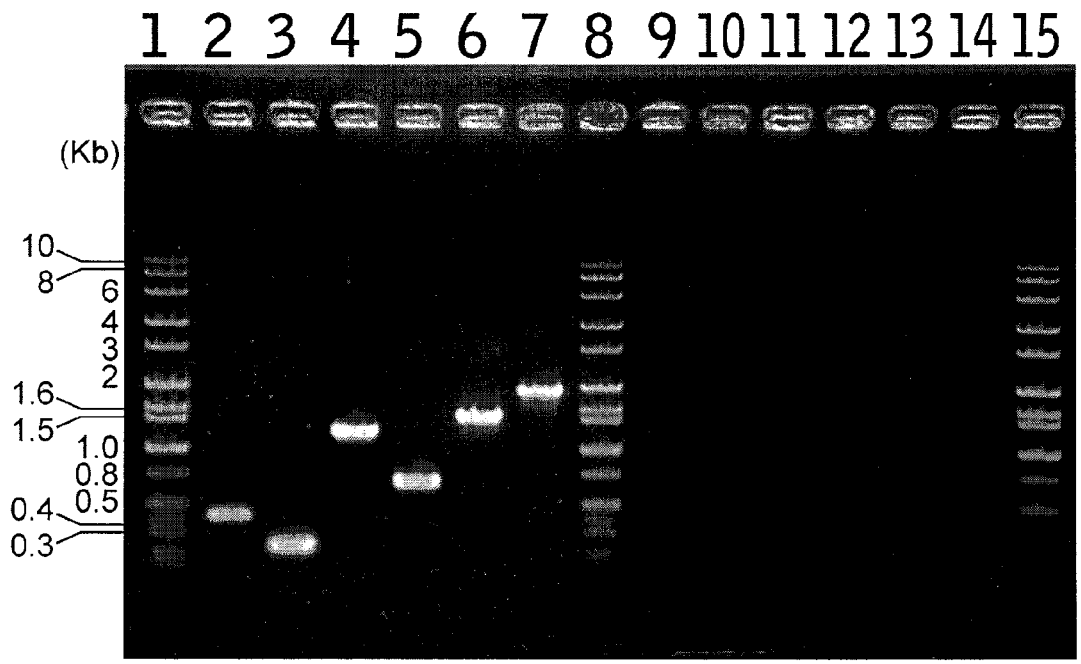
FIG. 6 is a diagram showing the results of detecting plasmids in the case where the PCR was conducted with primer sets A to F shown in Table 1, with the DNAs extracted from the strain MBE 131 and *Kocuria rosea* standard strain of Example 3 as templates.

In the PCR, LA taq polymerase (manufactured by TAKARA BIO INC.) was used. One cycle was a reaction with a thermal denaturation condition of 98 degrees Celsius for 30 seconds, an annealing condition of 62 degrees Celsius for 60 seconds, and a elongation condition of 72 degrees Celsius for two minutes. The cycle was repeated 30 times in total. The obtained PCR reactant was loaded into agarose gel electrophoresis. When the DNA solution obtained from the strain MBE 131 was used as a template, an amplified fragment was detected that was equal in size to what was calculated based on SEQ ID NO: 1. However, when the DNA solution obtained from the standard strain of *Kocuria rosea* was used as a template, no amplified fragment was detected (See FIG. 6). Incidentally, Table 2 shows the relationship between lanes, primer sets, and DNAs employed as templates in the case of FIG. 6.

TABLE 2

| Lane | Primer set | Template |
|---|---|---|
| 1 | | DNA size marker |
| 2 | A | DNA solution extracted from strain MBE131 (containing pKR100) |
| 3 | B | DNA solution extracted from strain MBE131 (containing pKR100) |
| 4 | C | DNA solution extracted from strain MBE131 (containing pKR100) |
| 5 | D | DNA solution extracted from strain MBE131 (containing pKR100) |
| 6 | E | DNA solution extracted from strain MBE131 (containing pKR100) |
| 7 | F | DNA solution extracted from strain MBE131 (containing pKR100) |

TABLE 2-continued

| Lane | Primer set | Template |
|---|---|---|
| 8 | | DNA size marker |
| 9 | A | DNA solution extracted from Kocuria rosea standard strain |
| 10 | B | DNA solution extracted from *Kocuria rosea* standard strain |
| 11 | C | DNA solution extracted from *Kocuria rosea* standard strain |
| 12 | D | DNA solution extracted from *Kocuria rosea* standard strain |
| 13 | E | DNA solution extracted from *Kocuria rosea* standard strain |
| 14 | F | DNA solution extracted from *Kocuria rosea* standard strain |
| 15 | | DNA size marker |

Figure 7:
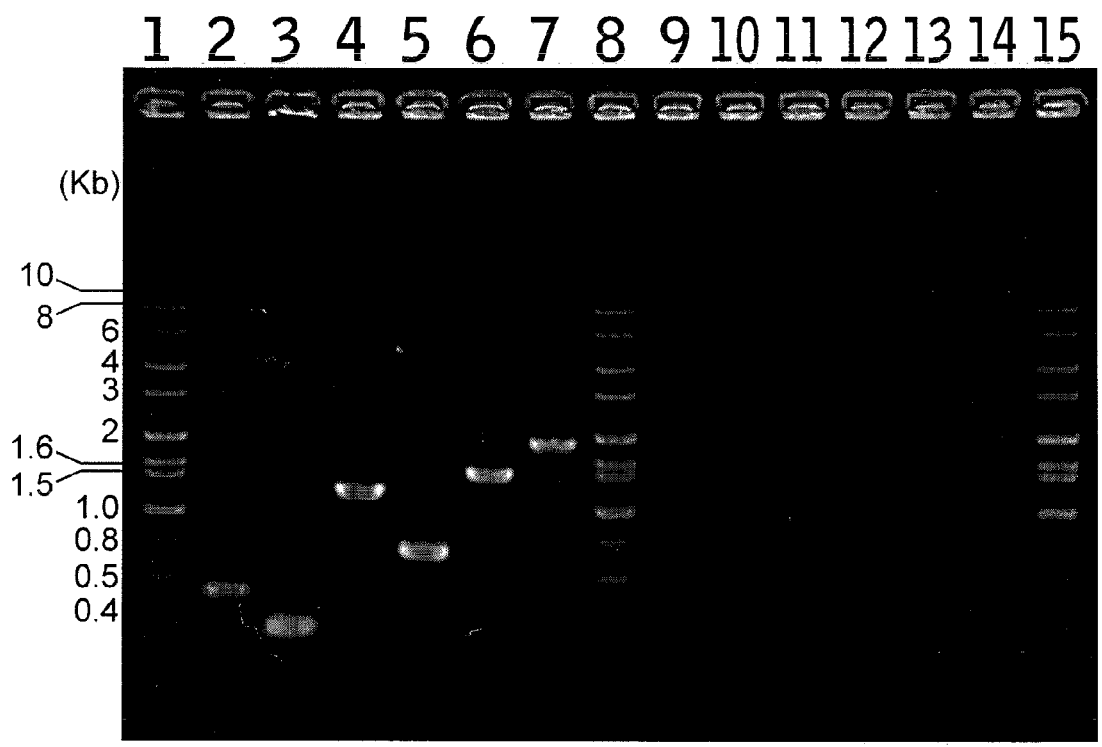
FIG. 7 is a diagram showing the results of detecting plasmids in the case where the PCR was conducted with primer sets A to F shown in Table 1, with the DNAs contained in the cell lysis solutions of the strain MBE 131 and *Kocuria rosea* standard strain of Example 3 as templates.

Furthermore, the strain MBE 131 or the standard strain of *Kocuria rosea* was suspended in the 0.1% TritonX solution containing 0.1 mg/mL of protease K; incubated at 65 degrees Celsius for 20 minutes; and then heated at 100 degrees Celsius for 10 minutes. In this manner, a cell lysis solution was prepared. The cell lysis solution, which was obtained from each bacterial strain, was employed as a template DNA solution. The PCR was carried out with the use of the above-described primer sets A-F (Table 1). In the PCR, LA taq polymerase (manufactured by TAKARA BIO INC.) was used. One cycle was a reaction with a thermal denaturation condition of 98 degrees Celsius for 30 seconds, an annealing condition of 62 degrees Celsius for 60 seconds, and a elongation condition of 72 degrees Celsius for two minutes. The cycle was repeated 30 times in total. The obtained PCR reactant was loaded into agarose gel electrophoresis. When the cell lysis solution obtained from the strain MBE 131 was employed as a template DNA solution, an amplified fragment was detected, which was equal in size to what was calculated based on SEQ ID NO: 1. However, when the cell lysis solution obtained from the standard strain of *Kocuria rosea* was employed as a template DNA solution, no amplified fragment was detected (See FIG. 7). It was found from the above results that there was no plasmid pKR100 in the standard strain of *Kocuria rosea*. Incidentally, Table 3 shows the relationship between lanes, primer sets, and DNAs used as templates in the case of FIG. 7.

TABLE 3

| Lane | Primer set | Template |
|---|---|---|
| 1 | | DNA size marker |
| 2 | A | Cell lysis solution of strain MBE131 |
| 3 | B | Cell lysis solution of strain MBE131 |
| 4 | C | Cell lysis solution of strain MBE131 |
| 5 | D | Cell lysis solution of strain MBE131 |
| 6 | E | Cell lysis solution of strain MBE131 |
| 7 | F | Cell lysis solution of strain MBE131 |
| 8 | | DNA size marker |
| 9 | A | Cell lysis solution of *Kocuria rosea* standard strain |
| 10 | B | Cell lysis solution of *Kocuria rosea* standard strain |
| 11 | C | Cell lysis solution of *Kocuria rosea* standard strain |
| 12 | D | Cell lysis solution of *Kocuria rosea* standard strain |
| 13 | E | Cell lysis solution of *Kocuria rosea* standard strain |
| 14 | F | Cell lysis solution of *Kocuria rosea* standard strain |
| 15 | | DNA size marker |

Example 5

Constitution of Shuttle Vector

A DNA fragment comprising a base sequence represented by the 7$^{th}$ to 3,170$^{th}$ of SEQ ID NO: 4 of plasmid pKR100 and a chloramphenicol resistance gene derived from *Staphyrococcus aureus* were linked to a multicloning site of pHY300PLK, thereby constituting shuttle vector pR6632 with respect to *Escherichia coli* bacteria. The transformation of *Kocuria* bacteria strain MBE131 was carried out by electroporation under the following conditions with the use of a plasmid prepared from a transformant of *Escherichia coli* bacteria HB101 having pR6632: Plasmid DNA 0.1 to 10 µg; Electric field intensity 6 to 25 kV/cm; Resistance 50 to 900Ω. The incubation time after pulse processing of cells was three hours at 30 degrees Celsius.

Figure 8:
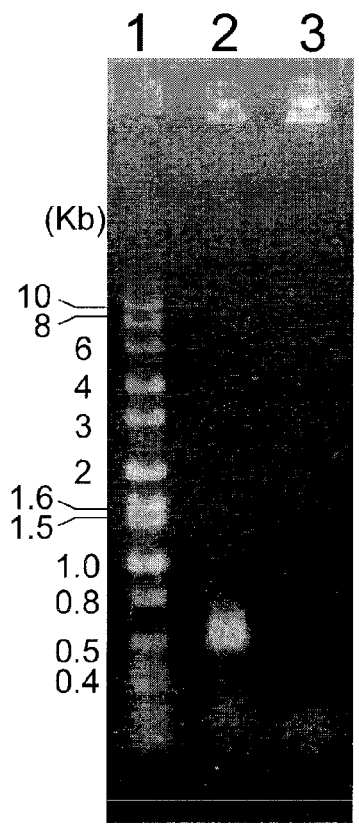
FIG. 8 is a diagram showing the results of detecting, through PCR, recombinant plasmid pR6632 introduced into a transformant of MBE131 in Example 5. Lane 1 shows a DNA size marker.

On the YTNM agar medium containing 2 µg/mL of chloramphenicol or 4 µg/mL of tetracycline, the above transformant was cultured at 30 degrees Celsius for five to seven days. A colony that had grown was suspended in the 0.1% TritonX solution containing 0.1 mg/mL of protease K; incubated at 65 degrees Celsius for 20 minutes; and then heated at 100 degrees Celsius for 10 minutes. In this manner, a cell lysis solution was prepared. With the obtained cell lysis solution as a template DNA solution, the PCR was carried out with the use of primer sets (primer sets made up of the base sequences disclosed in SEQ ID NO: s 21 and 22) complementary to the base sequence of a chloramphenicol resistance gene that pR6632 had. In the PCR here, a chloramphenicol resistance gene did not exist in wild-type strains of MBE131 and plasmid pHY300PLK. Therefore, it was possible to selectively detect the introduced pR6632. In the PCR, LA taq polymerase (manufactured by TAKARA BIO INC.) was used. One cycle was a reaction with a thermal denaturation condition of 98 degrees Celsius for 30 seconds, an annealing condition of 60 degrees Celsius for 60 seconds, and a elongation condition of 72 degrees Celsius for one minute. The cycle was repeated 30 times in total. The obtained PCR reactant was loaded into agarose gel electrophoresis. When the cell lysis solution obtained from the strain MBE 131 transformant was employed as a template DNA solution, an amplified fragment was detected, which was calculated from the base sequence of pR6632 (See Lane 2 of FIG. 8). By comparison, the same experiment was carried out with the use of a wild-type strain of MBE131, but no amplified fragment was detected (See Lane 3 of FIG. 8).

Figure 9:
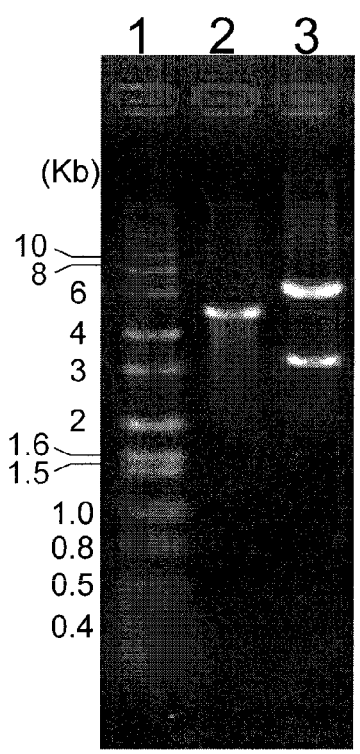
FIG. 9 is a diagram showing the results of confirming, through restriction enzyme digestion patterns, recombinant plasmid pR6632 introduced into a transformant of MBE131 in Example 5. Lane 1 shows a DNA size marker.

Meanwhile, the MBE131 transformant was cultured at 30 degrees Celsius on the YTNM medium for one day. A plasmid extraction operation was carried out with the use of a plasmid purification kit in a similar way to that in Example 1. With the use of the obtained DNA solution, *Escherichia coli* bacteria HB101 were transformed. From the transformant of *Escherichia coli* bacteria, a plasmid was prepared with the use of the same plasmid purification kit, and then loaded into agarose gel electrophoresis after being digested with restriction enzyme HindIII (See FIG. 9). By comparison, pHY300PKL digested by the same restriction enzyme was simultaneously loaded into agarose gel electrophoresis (Lane 2 of FIG. 9). As a result, on the basis of the restriction enzyme digestion pattern, it was found that a plasmid that the obtained MBE131 transformant had was pR6632 (Lane 3 of FIG. 9).

It was seen from the above results that plasmid pR6632 was replicated and retained in the strain MBE 131. The chloramphenicol resistance of the strain MBE 131 containing pKR100 was less than 1 µg/mL on the YTNM solid medium. On the other hand, the strain MBE 131 transformed by pR6632 showed resistance to 50 µg/mL of chloramphenicol. Moreover, pR6632 includes a tetracycline gene derived from *Enterococcus faecalis*. The strain MBE 131 containing pKR100 had a tetracycline resistance of less than 3 µg/mL. On the other hand, the strain MBE 131 transformed by pR6632 showed resistance to 100 µg/mL of tetracycline. Accordingly, it was considered that a plasmid containing pKR100 would function as a vector serving to hold and express heterologous foreign genes in the strain MBE 131.

Example 6

Identification of Region for Replication

Figure 4:
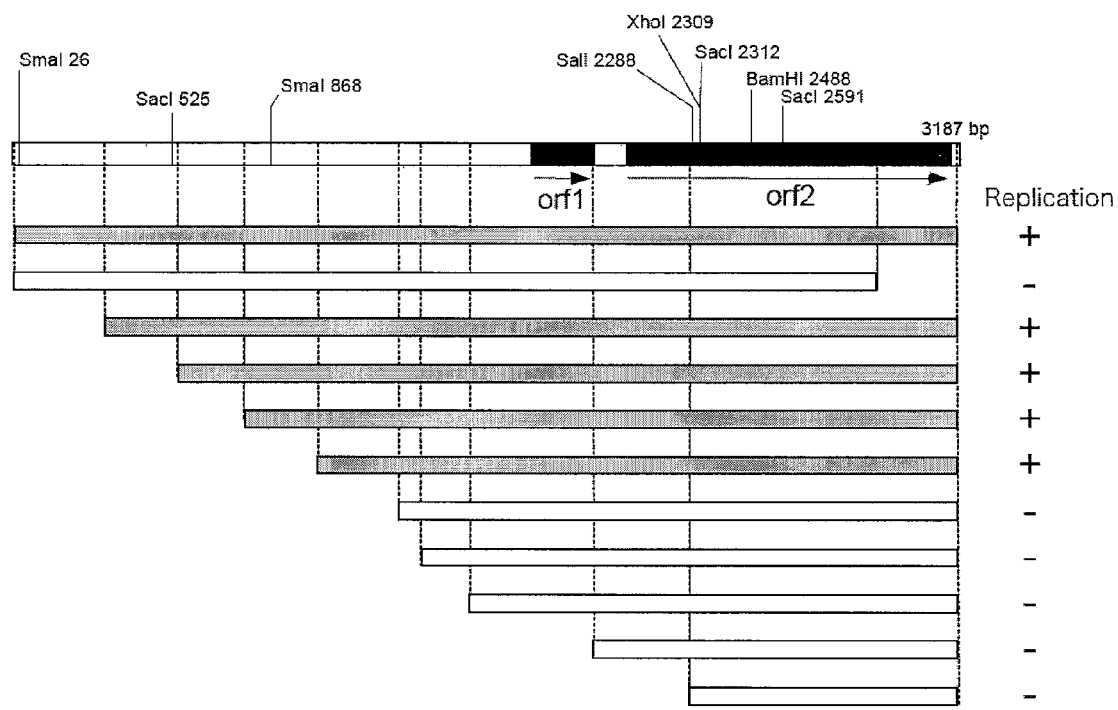
FIG. 4 is a diagram showing the results of investigating a DNA replication region of pKR100 described in Example 6; among the plasmids comprising DNA fragments shown in FIG. 4, the symbol "+" indicates a plasmid that was confirmed to be replicated, and the symbol "−" indicates a plasmid that was not confirmed to be replicated.

Various DNA fragments comprising part of plasmid pKR100 were amplified by PCR. The above chloramphenicol resistance gene was linked to a multicloning site of pHY300PLK. Furthermore, the fragments shown in FIG. 4 were each linked thereto. In each of the plasmids constituted, *Escherichia coli* bacteria HB101 were transformed. From the transformant of *Escherichia coli* bacteria HB101, plasmids were prepared. With the use of the prepared plasmid, the strain MBE 131 was transformed by the above-described method. As a result, when a plasmid that had a fragment comprising the base sequence of the $1,031^{st}$ to $3,170^{th}$ of SEQ ID NO: 1 was employed, the strain MBE 131 could be transformed (See FIG. 4). Therefore, it can be said that a region represented by the base sequence of the $1,031^{st}$ to $3,170^{th}$ shown in SEQ ID NO: 1 is a region that plays a role in the replication and retention of the plasmid in the strain MBE 131. Incidentally, a fragment comprising the base sequence of the $1,031^{st}$ to $3,170^{th}$ of SEQ ID NO: 1 was obtained in the following manner. With plasmid pKR100 as a template, the PCR was carried out with the use of one primer set, which was selected from among the primer sets consisting of forward and reverse primers ranging from G to Q as shown in Table 4.

Example 7

Preparation of Transformant with Different Species as Host Cell

With the use of plasmid pR6632, *Kocuria rhizophila* DC2201 (NBRC103217), a different species of bacteria of the genus *Kocuria*, was transformed. The transformant was cultured on the YTNM agar medium containing 2 µg/mL of chloramphenicol or 4 µg/mL of tetracycline at 30 degrees Celsius for five to seven days. A colony that had grown was suspended in the 0.1% TritonX solution containing 0.1 mg/mL of protease K; incubated at 65 degrees Celsius for 20 minutes; and then heated at 100 degrees Celsius for 10 minutes. In this manner, a cell lysis solution was prepared. With the obtained cell lysis solution as a template DNA solution, the PCR was carried out with the use of primer sets (forward and reverse primers made up of the base sequences disclosed in SEQ ID NO:s 21 and 22) complementary to the base sequence of a chloramphenicol resistance gene that pR6632 had, and primer sets (forward and reverse primers made up of the base sequences disclosed in SEQ ID NO: s 43 and 44) complementary to the base sequence of a tetracycline resistance gene.

The chloramphenicol resistance gene and the tetracycline resistance gene did not exist on the DC2201 strain genome. Therefore, it was possible to selectively detect pR6632. In the PCR, LA taq polymerase (manufactured by TAKARA BIO INC.) was used. One cycle was a reaction with a thermal denaturation condition of 98 degrees Celsius for 30 seconds, an annealing condition of 60 degrees Celsius for 60 seconds, and a elongation condition of 72 degrees Celsius for one minute. The cycle was repeated 30 times in total. The obtained PCR reactant was loaded into agarose gel electrophoresis. When the cell lysis solution obtained from the

TABLE 4

| Set No. | Forward primer | Reverse primer |
| --- | --- | --- |
| G | ATTAAAGCTTCCAAGGTGAGGGGACGC | GTCCACAAGCTTGGAGACTGTTTCAGAG |
| H | ATTAAAGCTTCCAAGGTGAGGGGACGC | AAAAAAGCTTCGGCGGCCAGGTCGGTGTTGATGC |
| I | TTTTAAGCTTCGGGTGAGGCAACCAGAAC | GTCCACAAGCTTGGAGACTGTTTCAGAG |
| J | ATTGGAAGCTTCGTGAGACCAGTCC | GTCCACAAGCTTGGAGACTGTTTCAGAG |
| K | TTTTAAGCTTGGACTAGCCGGCGTTGC | GTCCACAAGCTTGGAGACTGTTTCAGAG |
| L | AAGGGTAAGCTTCGGTCAGGCTGGACGGTGCGTGG | GTCCACAAGCTTGGAGACTGTTTCAGAG |
| M | AAGGAAGCTTGTGCGCTAAGCCGTGTACG | GTCCACAAGCTTGGAGACTGTTTCAGAG |
| O | TTTTAAGCTTCTCGTACCCCGCGTCTCAG | GTCCACAAGCTTGGAGACTGTTTCAGAG |
| P | CACCCGAAGCTTCTCGTGTGAGCGCTGCG | GTCCACAAGCTTGGAGACTGTTTCAGAG |
| Q | AGGTTAAGCTTGGTCCGTCAGTAGGCCAGTG | GTCCACAAGCTTGGAGACTGTTTCAGAG |

In the PCR, LA taq polymerase (manufactured by TAKARA BIO INC.) was used. One cycle was a reaction with a thermal denaturation condition of 94 to 98 degrees Celsius for 15 to 30 seconds, an annealing condition of 55 to 68 degrees Celsius for 15 to 60 seconds, and a elongation condition of 72 degrees Celsius for two to five minutes. The cycle was repeated 30 times in total.

Figure 10:
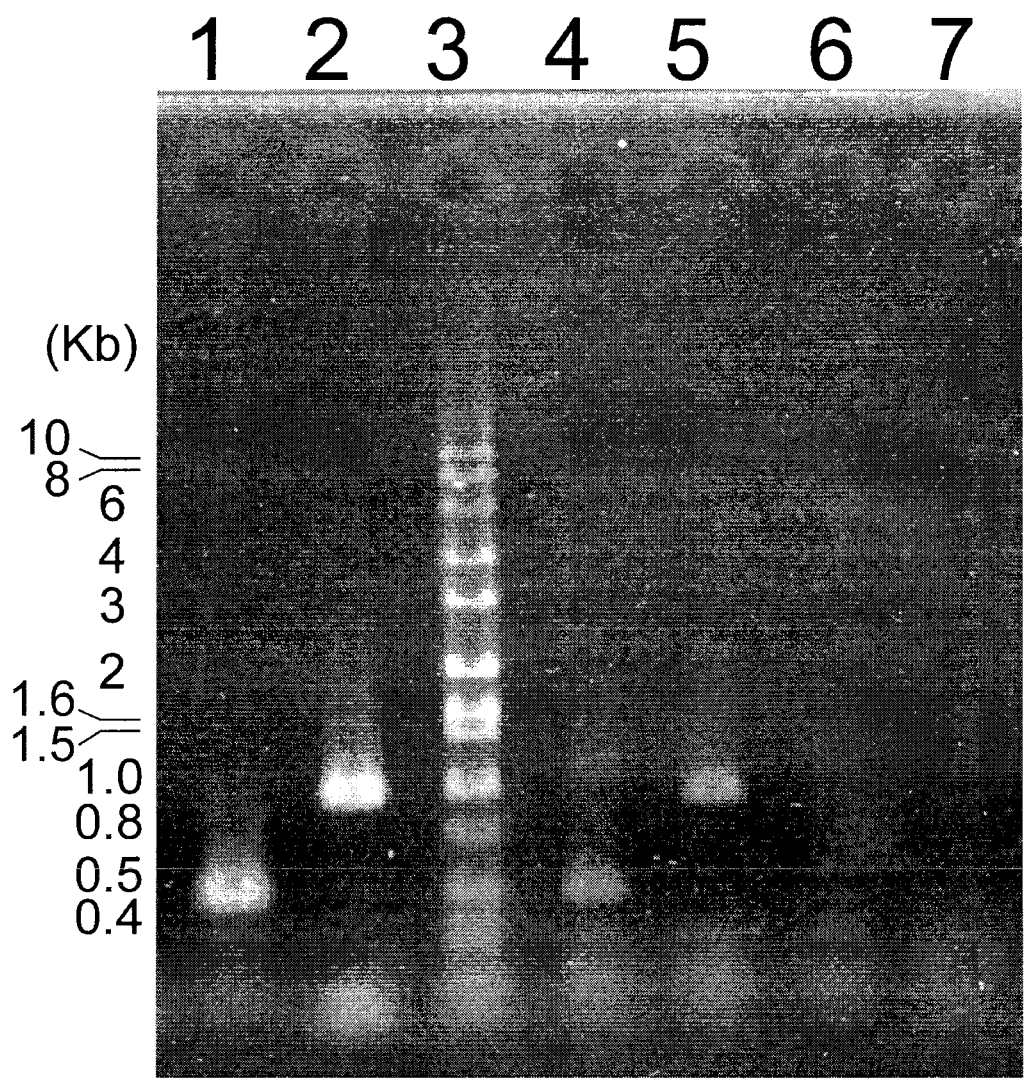
FIG. 10 is a diagram showing the results of detecting plasmid pR6632 introduced into DC2201 strain by means of PCR as mentioned below in Example 7. Lane 3 shows a DNA size marker.

DC2201 transformant was employed as a template DNA solution, an amplified fragment was detected, which was calculated from the base sequence of pR6632 (See Lanes 1 and 2 of FIG. 10). Moreover, the amplified fragment was nearly equal in size to a PCR amplified fragment obtained when the strain MBE 131 transformant was employed (See Lanes 4 and 5 of FIG. 10). By comparison, the same experiment was carried out with the use of a wild-type strain of DC2201, but no amplified fragment was detected (See Lanes 6 and 7 of FIG. 10). Accordingly, it was found that the amplified fragment detected was derived from the introduced plasmid pR6632. As a result, it was seen that plasmid pR6632 was replicated and retained even in the DC2201 strain.

Therefore, it was considered that plasmid pR6632 could be replicated and retained even in other different species of bacteria of the genus *Kocuria*. The chloramphenicol resistance of the DC2201 strain containing no plasmid was less than 1 μg/mL on the YTNM solid medium. On the other hand, the DC2201 strain transformed by pR6632 showed resistance to 10 μg/mL of chloramphenicol. Accordingly, it was considered that a plasmid that comprised a region playing a role in the replication of pKR100 functioned as a vector serving to hold and express heterologous foreign genes even in different species of bacteria of the genus *Kocuria*.

Example 8

Functional Analysis of Non-Protein Coding Region in pKR100

Figure 12:
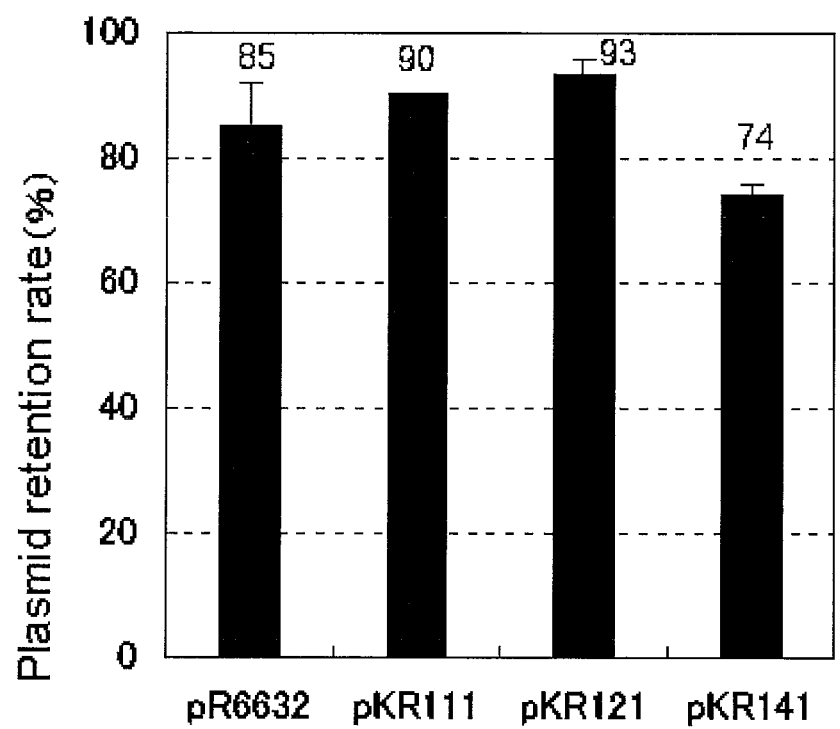
FIG. 12 is a diagram showing a plasmid retention rate (%) in bacteria of the genus *Kocuria*, with each type of synthetic plasmid in the case of Example 8.

In order to confirm a function of a DNA base sequence that did not code a protein that pKR100 had, the experiment as described below was performed. Plasmids pKR111, pKR121, and pKR141 comprising a DNA fragment which lacked part of pKR100 were constituted. The plasmids had a chloramphenicol resistance gene as a selection marker in the same manner as pR6632. pKR111 comprised a DNA fragment derived from the $312^{th}$ to $3,170^{th}$ of pKR100. pKR121 comprised a DNA fragment derived from the $559^{th}$ to $3,170^{th}$ of pKR100. pKR141 comprised a DNA fragment derived from the $1,031^{st}$ to $3,170^{th}$ of pKR100. As in the case of pR6632, pKR111 and pKR121 had two sets of unique sequences made up of the direct repeat and the inverted repeat, which were made up of approximate repeat motif sequences. However, pKR141 had only one set of them. The transformants that each contained each of the plasmids, MBE131 (pR6632), MBE131 (pKR111), MBE131 (pKR121), and MBE131 (pKR141), were cultured at 25 degrees Celsius for 20 generations in the YTNM medium containing no antibiotic. After the culturing, the culture solution was applied to the YTNM agar medium containing no antibiotic, and was cultured at 25 degrees Celsius for three days to form a single colony. Each of the colonies that had grown on the solid agar media was simultaneously picked up on the YTNM agar media containing no antibiotic and the solid agar media containing chloramphenicol. Relative to the number of colonies that had grown on the solid agar media containing no antibiotic, the number of colonies that had grown on the solid agar media containing chloramphenicol was calculated as plasmid retention rate (%) (See FIG. 12). As a result, it was found that pKR141, which had only one set of unique sequences made up of the direct repeat and the inverted repeat that are made up of approximate repeat motif sequences, had a lower level of the stability of plasmid, compared with other test plasmids. That is, it was found that the base sequence of the $559^{th}$ to $1,031^{st}$ of pKR100 had a function associated with retaining a plasmid in a stable manner. Moreover, the plasmid that lacked the direct repeat that existed in pKR141 was not replicable in the strain MBE 131 (see Example 6 as explained in the above-described example). Therefore, it can be determined that the unique sequences made up of the direct repeat and the inverted repeat play an important role in the replication and stable retention of pKR100. Moreover, it can be determined that the $559^{th}$ to $3,170^{th}$ bases of pKR100 play an important role in the replication and stability of plasmids.

The *Kocuria* sp. strain MBE131 has been deposited in the International Patent Organism Depositary of the National Institute of Advanced Industrial Science and Technology (Tsukuba Central 6, 1-1, Higashi 1-chome Tukuba-shi, Ibaraki-ken 305-8566 Japan) with Receipt Number FERM P-21885 on Jan. 6, 2010.

The base sequences disclosed in the present application are listed below:

```
region of orf 1 in pKR100
                                                        [SEQ ID NO: 1]
ATGGGCGACCCTCAGCTTGTAATGGGCTTTTTCCAGGTCTTCCTTCGTGCCTTTCTCGTACA

GAGCGTCTGCTTCGAGAAGGGCCCATTCCGCTTCGACAAACTGCCGGGCAAGAAGTTTTTTG

CTGGATGGCTTAGTCATGGCAAGGAACGTAGCTGCCGAAGTAGTGAAGGCTGTACAGATCCG

ACGCGGTTCGCGCGGGTCCGTCAGTAG region of orf2 in pKR100
                                                        [SEQ ID NO: 2]
GTGACCAGTGTAGGCACGCACCTTCCCTCGTCCACCAGCCCCGCCGCAACACGGCAGGCGGC

TGTTCGGCAGGCATTTGTTAACCATTTAGGCGTGCGCCACGTGCGTGTGGCGGCCACCAAGA

ACGGTGCGCCGCGCACCGTTCCCATTGAGGCGTTAGGCGAGTTCGCCTTTTGGACGCCACCG

GCCTGGCCCAACCTCGGATTGCTGACTATTGACGTCGACCGGGATGCGGCCGTGCTCGAGCT

CTTCGCCGCCCCTGCCCTGCCGCATGTGGTCGTGGAGACCCCCGCGGGGCCCAAGCGGTGT

GGCTGATCGACCGAGTACACACCGGCCCGAACGCCCGCCCGCACCCGATCGCCTATGCCGAA

ACCGTAGGAAGCGCTTTGCGTGCCTCCCTGGATGGAGACTCGGCCGTGGATCCATTGCGCCC

GGTACGTACCCGTAACCCCTGCTACAGACCTGCACAGCGCGATGTGTTCACCACTGCCCGCC

CGCTAACGGCGCCCTACCGTCTCGGAGAGCTCCAGAAATCCCTGGATGCTGCTGGAGCATGG

CCAACACGTCCTGAGCGCTCTCAGGCCCGTGGAAGGGCGCAGAAGGCCGTTGACGGAGTGTT

CGTGGGCCGTAACGACGCCGTCAACCGCTCCACCTGGCTGACCGTGCGCTACGGACTCGAAA
```

-continued

```
ATGGTTCCGTGACTCACTGGACCGATGCCGACGTGCTGGAGCTGGCCCATGGCATTAACGAG

GCCGTCGCTGCTGAGCAAGGCGTGCCGCCCTTACCCGAGGATCAAGTGCGCGACTTGGCTGT

CTCGATCTGCCGGCATCAACACCGACCTGGCCGCCGAGCCATCTCCGGACAAGGCTCGGCCA

CCGCCCGCGCCCTCGGCGCTAAAGGCGGCGCAGCCCGTTCCGAGGCCAAAACCATTAGCGGG

CGGCGCAACGTGGGCAAGGCGACCGCTGTGCGTTCCGCATCCGCGGCCTTGCGTTCTGAGAG

CATCCGAATCCTGGCCGAGCAAGGGCACACCTACGAGGCCATTGCCGCCGCTGTCGGATGCT

CCACTAAGACCGTTCAGCGTGCTCTTCGCGACCTCTGA
``` replication region in pKR100

[SEQ ID NO: 3]

```
CGGTCAGGCTGGACGGTGCGTGGTCATAAACCGTGGGTCGGTTCGGAGAGCCGGGGGTGGC

TTCCTATCGTCGTGAGATGAGCAGAGAACGCTATGAGCCGATGAGTGAGGCCCGGTTGGAAG

TCGCTTGGATGGTCGTGTTGCTGGGGTGTGCGCTGGTTCTTATGGGTGGGGTGGCCCTGGAT

GTGTTGATCGATCATCTCGCTGTCAGCTTCGCCTTGGCGGGGGTGCCGAGTGTGTTGGTGGT

GGCGGTGTTGTGGCGGCGGCACGTGCGCTAAGCCGTGTACGGGCACAGAAAAAGCCGGGTGG

TAGAGCCCGGCTTTTTCCGTGGGGAGAGTCTCGTACCCCGCGTCTCAGTGTCCTGCACACC

GGTCGTGATGCCTACTGCCGCTACACGGAGCAAAGCTATGCGTTATGTGCCATAAACGCGGA

TCGCCCTTCGTCCAGCTCGTGGAGCTGGCTGAGTGCCTATGTGCCATAGGCGGGCGGGGGCA

CCCGAGCGGGCTCGTGTGAGCGCTGCGCTGGGCATAGGGAAGGCCGGGCGCTAGCCCAGCCC

TCCATGGGGCAGAGGGCCCCGTGGTGTTGAGAGTGGCGAGCCCTACTGAGGGTCCTCGAAG

GCGTCGGGGCGCTTCGTGTCCTCTTCAGTTTTTGATCCCTGGCGTCCTGAACTTCGTTCGC

GACTGCCTCCGGGGTGCCGGTGGCAAGGAGAGCATGCACATGGGCGACCCTCAGCTTGTAAT

GGGCTTTTTCCAGGTCTTCCTTCGTGCCTTTCTCGTACAGAGCGTCTGCTTCGAGAAGGGCC

CATTCCGCTTCGACAAACTGCCGGGCAAGAAGTTTTTTGCTGGATGGCTTAGTCATGGCAAG

GAACGTAGCTGCCGAAGTAGTGAAGGCTGTACAGATCCGACGCGGTTCGCGCGGGTCCGTCA

GTAGGCCAGTGATGGGCCATAGGGTGACCAGGAAAGAGTTGAGCCCCGGAGATTCCACCCTC

CGGGGCTCGACTTCCCCGATTGATAGCGGCAATCAGGAGAAGCCTTGTGACCAGTGTAGGCA

CGCACCTTCCCTCGTCCACCAGCCCCGCCGCAACACGGCAGGCGGCTGTTCGGCAGGCATTT

GTTAACCATTTAGGCGTGCGCCACGTGCGTGTGGCGGCCACCAAGAACGGTGCGCCGCGCAC

CGTTCCCATTGAGGCGTTAGGCGAGTTCGCCTTTTGGACGCCACCGGCCTGGCCCAACCTCG

GATTGCTGACTATTGACGTCGACCGGGATGCGGCCGTGCTCGAGCTCTTCGCCGCCCTGCC

CTGCCGCATGTGGTCGTGGAGACCCCCGCGGGGCCCAAGCGGTGTGGCTGATCGACCGAGT

ACACACCGGCCCGAACGCCCGCCCGCACCCGATCGCCTATGCCGAAACCGTAGGAAGCGCTT

TGCGTGCCTCCCTGGATGGAGACTCGGCCGTGGATCCATTGCGCCCGGTACGTACCCGTAAC

CCCTGCTACAGACCTGCACAGCGCGATGTGTTCACCACTGCCCGCCCGCTAACGGCGCCCTA

CCGTCTCGGAGAGCTCCAGAAATCCCTGGATGCTGCTGGAGCATGGCCAACACGTCCTGAGC

GCTCTCAGGCCCGTGGAAGGGCGCAGAAGGCCGTTGACGGAGTGTTCGTGGGCCGTAACGAC

GCCGTCAACCGCTCCACCTGGCTGACCGTGCGCTACGGACTCGAAAATGGTTCCGTGACTCA

CTGGACCGATGCCGACGTGCTGGAGCTGGCCCATGGCATTAACGAGGCCGTCGCTGCTGAGC

AAGGCGTGCCGCCCTTACCCGAGGATCAAGTGCGCGACTTGGCTGTCTCGATCTGCCGGCAT

CAACACCGACCTGGCCGCCGAGCCATCTCCGGACAAGGCTCGGCCACCGCCCGCGCCCTCGG

CGCTAAAGGCGGCGCAGCCCGTTCCGAGGCCAAAACCATTAGCGGGCGGCGCAACGTGGGCA
```

-continued
AGGCGACCGCTGTGCGTTCCGCATCCGCGGCCTTGCGTTCTGAGAGCATCCGAATCCTGGCC
GAGCAAGGGCACACCTACGAGGCCATTGCCGCCGCTGTCGGATGCTCCACTAAGACCGTTCA
GCGTGCTCTTCGCGACCTCTGAAACAGTCTCC pKR100
[SEQ ID NO: 4]
ATAAGCCCAAGGTGAGGGACGCTCCCCGGGCCTCTCAGCCCCCCCTCTGAGGGCTCCTGCG
GGCACCTCCTACGATCCTCCGAACAGCCCTGATCGTCACACCTCATGCATCATTCGATGAGC
CAGGTCTAGGTGACCAAACGCAGGCGGCCACAGACTCAGCTGCACTCTCATCGTGAGGTGCC
CAGAGCGTCGCAACAAGGCACCGACCCAGCCTCAATTTTCATCCGCCGGCCTTAACGGCGAC
CGTCACTGTTGATGACTTTTGCTGTCCTCGAATCACCCTTCGCGGGTGAGGGGTAACCCGCT
TCGGGTGAGGCAACCAGAACGGGTCCCTGTGCTCGGCTATGTGGTCGAGCAGGTGCCTGGTG
GGGTGGCGTGGTCGTTGTCGGCGGGCCGGTTTCGGGCGCGCTGGGGTGACCTAGCTGTGCGC
ACCGAGGACCGGTGCGAAGGACAAGATGAGCGTCTTTCCCGAGGGCCGGCCAAAGAATGCAA
GAGGTGTGACGACTTGGATCAGAGTTCGGAGCTCCGACGCATTGGGAGGTGATTGGGTGCAG
CGTGAGACCAGTCCGTAGCGTTTGACGAATGCAAATGCGACGCGGGGACCAGGAGGCTAGAC
ATCGTCGAGATATGGCTTGGATTCTGGTGCTGCTGGCTGGAGTGCAGGTGGGTTTGCTGGCG
ACGGTGATCGGTGTCTTGGTCGAGGACCTCGTGGTGGGCACTGTCGTTGCTTTGGTTCCTGG
GGCTGTGGTGGTGGGCTGTGGTGGCGGCGGTTTTTGGACTAGCCGGCGTTGCTGGGCATGG
AAAAAGCCGGCTGCTGCCCGGCTTTTTCTTCTGGGAGGCGGGGCCTGGTCAACCGGGCCTC
CCGGGAAGCGGTGGTGTGAGCACGTCAGTTCCCGCCTCCAGTGTTGGCCGTTCTTCGGTTTG
TTCCCAAAAGTGACGGCGATGGGTGGGTGGAAGGTCCCGTCCAGGTCTGATTTGCCGGCACA
GGTTGCTGGGCCGGGGTTGTCCCCGTAGGGGTCTGTCCCGGTCAGGCTGGACGGTGCGTGGT
CATAAACCGTGGGTCGGTTCGGAGAGCCGGGGGGTGGCTTCCTATCGTCGTGAGATGAGCAG
AGAACGCTATGAGCCGATGAGTGAGGCCCGGTTGGAAGTCGCTTGGATGGTCGTGTTGCTGG
GGTGTGCGCTGGTTCTTATGGGTGGGGTGGCCCTGGATGTGTTGATCGATCATCTCGCTGTC
AGCTTCGCCTTGGCGGGGGTGCCGAGTGTGTTGGTGGTGGCGGTGTTGTGGCGGCGGCACGT
GCGCTAAGCCGTGTACGGGCACAGAAAAAGCCGGGTGGTAGAGCCCGGCTTTTTCCGTGGGG
GAGAGTCTCGTACCCCGCGTCTCAGTGTCCTGCACACCGGTCGTGATGCCTACTGCCGCTAC
ACGGAGCAAAGCTATGCGTTATGTGCCATAAACGCGGATCGCCCTTCGTCCAGCTCGTGGAG
CTGGCTGAGTGCCTATGTGCCATAGGCGGCGGGGGCACCCGAGCGGGCTCGTGTGAGCGCT
GCGCTGGGCATAGGGAAGGCCGGGCGCTAGCCCAGCCCTCCATGGGGGCAGAGGGCCCCGTG
GTGTTGAGAGTGGCGAGCCCTACTGAGGGTCCTCGAAGGCGTCGGGGGCGCTTCGTGTCCTC
TTCAGTTTTTGATCCCTGGCGTCCTGAACTTCGTTCGCGACTGCCTCCGGGGTGCCGGTGGC
AAGGAGAGCATGCACATGGGCGACCCTCAGCTTGTAATGGGCTTTTTCCAGGTCTTCCTTCG
TGCCTTTCTCGTACAGAGCGTCTGCTTCGAGAAGGGCCCATTCCGCTTCGACAAACTGCCGG
GCAAGAAGTTTTTTGCTGGATGGCTTAGTCATGGCAAGGAACGTAGCTGCCGAAGTAGTGAA
GGCTGTACAGATCCGACGCGGTTCGCGCGGGTCCGTCAGTAGGCCAGTGATGGGCCATAGGG
TGACCAGGAAAGAGTTGAGCCCCGGAGATTCCACCCTCCGGGGCTCGACTTCCCCGATTGAT
AGCGGCAATCAGGAGAAGCCTTGTGACCAGTGTAGGCACGCACCTTCCCTCGTCCACCAGCC
CCGCCGCAACACGGCAGGCGGCTGTTCGGCAGGCATTTGTTAACCATTTAGGCGTGCGCCAC
GTGCGTGTGGCGGCCACCAAGAACGGTGCGCCGCGCACCGTTCCCATTGAGGCGTTAGGCGA
GTTCGCCTTTTGGACGCCACCGGCCTGGCCCAACCTCGGATTGCTGACTATTGACGTCGACC -continued

```
GGGATGCGGCCGTGCTCGAGCTCTTCGCCGCCCCTGCCCTGCCGCATGTGGTCGTGGAGACC

CCCCGCGGGGCCCAAGCGGTGTGGCTGATCGACCGAGTACACACCGGCCCGAACGCCCGCCC

GCACCCGATCGCCTATGCCGAAACCGTAGGAAGCGCTTTGCGTGCCTCCCTGGATGGAGACT

CGGCCGTGGATCCATTGCGCCCGGTACGTACCCGTAACCCCTGCTACAGACCTGCACAGCGC

GATGTGTTCACCACTGCCCGCCCGCTAACGGCGCCCTACCGTCTCGGAGAGCTCCAGAAATC

CCTGGATGCTGCTGGAGCATGGCCAACACGTCCTGAGCGCTCTCAGGCCCGTGGAAGGGCGC

AGAAGGCCGTTGACGGAGTGTTCGTGGGCCGTAACGACGCCGTCAACCGCTCCACCTGGCTG

ACCGTGCGCTACGGACTCGAAAATGGTTCCGTGACTCACTGGACCGATGCCGACGTGCTGGA

GCTGGCCCATGGCATTAACGAGGCCGTCGCTGCTGAGCAAGGCGTGCCGCCCTTACCCGAGG

ATCAAGTGCGCGACTTGGCTGTCTCGATCTGCCGGCATCAACACCGACCTGGCCGCCGAGCC

ATCTCCGGACAAGGCTCGGCCACCGCCCGCGCCCTCGGCGCTAAAGGCGGCGCAGCCCGTTC

CGAGGCCAAAACCATTAGCGGGCGGCGCAACGTGGGCAAGGCGACCGCTGTGCGTTCCGCAT

CCGCGGCCTTGCGTTCTGAGAGCATCCGAATCCTGGCCGAGCAAGGGCACACCTACGAGGCC

ATTGCCGCCGCTGTCGGATGCTCCACTAAGACCGTTCAGCGTGCTCTTCGCGACCTCTGAAA

CAGTCTCCGTCGAGGTGGACATTTC

ORF2 coded by orf2 in pKR100
                                                      [SEQ ID NO: 5]
MTSVGTHLPSSTSPAATRQAAVRQAFVNHLGVRHVRVAATKNGAPRTVPIEALGEFAFWTPP

AWPNLGLLTIDVDRDAAVLELFAAPALPHVVVETPRGAQAVWLIDRVHTGPNARPHPIAYAE

TVGSALRASLDGDSAVDPLRPVRTRNPCYRPAQRDVFTTARPLTAPYRLGELQKSLDAAGAW

PTRPERSQARGRAQKAVDGVFVGRNDAVNRSTWLTVRYGLENGSVTHWTDADVLELAEGINE

AVAAEQGVPPLPEDQVRDLAVSICRHQHRPGRRAISGQGSATARALGAKGGAARSEAKTISG

RRNVGKATAVRSASAALRSESIRILAEQGHTYEATAAAVGCSTKTVQRALRDL

ORF1 coded by orf1 in pKR100
                                                      [SEQ ID NO: 6]
MGDPQLVMGFFQVFLRAFLVQSVCFEKGPFREDKLPGKKFFAGWLSHGKERSCRSSEGCTDP

TRFARVRQ

Forward primer for phylogenetic analysis of strain MBE131
                                                      [SEQ ID NO: 7]
AGAGTTTGATCCTGGCTCAG Reverse primer for phylogenetic analysis of strain MBE131
                                                      [SEQ ID NO: 8]
AAAGGAGGTGATCCAGCC Forward primer of the set A indicated in Table 1
                                                      [SEQ ID NO: 9]
TGGTGGCGGTGTTGTG Reverse primer of the set A indicated in Table 1
                                                     [SEQ ID NO: 10]
TCGCGAACGAAGTTCAGG Forward primer of the set B indicated in Table 1
                                                     [SEQ ID NO: 11]
GCCGGTGGCAAGGAGAGCATGCACATGGGCGACCCTC Reverse primer of the set A indicated in Table 1
                                                     [SEQ ID NO: 12]
CACTGGCCTACTGACGGACC Forward primer of the set C indicated in Table 1
                                                     [SEQ ID NO: 13]
GGTCCGTCAGTAGGCCAGTG
```

-continued

Reverse primer of the set C indicated in Table 1
[SEQ ID NO: 14]
GGAGACTGTTTCAGAG Forward primer of the set D indicated in Table 1
[SEQ ID NO: 15]
TGGTGGCGGTGTTGTG Reverse primer of the set D indicated in Table 1
[SEQ ID NO: 16]
CACTGGCCTACTGACGGACC Forward primer of the set E indicated in Table 1
[SEQ ID NO: 17]
GCCGGTGGCAAGGAGAGCATGCACATGGGCGACCCTC Reverse primer of the set E indicated in Table 1
[SEQ ID NO: 18]
GGAGACTGTTTCAGAG Forward primer of the set F indicated in Table 1
[SEQ ID NO: 19]
TGGTGGCGGTGTTGTG Reverse primer of the set F indicated in Table 1
[SEQ ID NO: 20]
GGAGACTGTTTCAGAG Forward primer complementary to the base sequence of a
chloramphenicol resistance gene that pR6632 had
[SEQ ID NO: 21]
GTTACAATAGCGACGGAGAG Reverse primer complementary to the base sequence of a
chloramphenicol resistance gene that pR6632 had
[SEQ ID NO: 22]
AGGTTAGTGACATTAGAAAACC Forward primer of the set G indicated in Table 4
[SEQ ID NO: 23]
ATTAAAGCTTCCAAGGTGAGGGGACGC Reverse primer of the set G indicated in Table 4
[SEQ ID NO: 24]
GTCCACAAGCTTGGAGACTGTTTCAGAG Forward primer of the set H indicated in Table 4
[SEQ ID NO: 25]
ATTAAAGCTTCCAAGGTGAGGGGACGC Reverse primer of the set H indicated in Table 4
[SEQ ID NO: 26]
AAAAAAGCTTCGGCGGCCAGGTCGGTGTTGATGC Forward primer of the set I indicated in Table 4
[SEQ ID NO: 27]
TTTTAAGCTTCGGGTGAGGCAACCAGAAC Reverse primer of the set I indicated in Table 4
[SEQ ID NO: 28]
GTCCACAAGCTTGGAGACTGTTTCAGAG Forward primer of the set J indicated in Table 4
[SEQ ID NO: 29]
ATTGGAAGCTTCGTGAGACCAGTCC Reverse primer of the set J indicated in Table 4
[SEQ ID NO: 30]
GTCCACAAGCTTGGAGACTGTTTCAGAG Forward primer of the set K indicated in Table 4
[SEQ ID NO: 31]
TTTTAAGCTTGGACTAGCCGGCGTTGC Reverse primer of the set K indicated in Table 4
[SEQ ID NO: 32]
GTCCACAAGCTTGGAGACTGTTTCAGAG Forward primer of the set L indicated in Table 4
[SEQ ID NO: 33]
AAGGGTAAGCTTCGGTCAGGCTGGACGGTGCGTGG Reverse primer of the set L indicated in Table 4
[SEQ ID NO: 34]
GTCCACAAGCTTGGAGACTGTTTCAGAG Forward primer of the set M indicated in Table 4
[SEQ ID NO: 35]
AAGGAAGCTTGTGCGCTAAGCCGTGTACG Reverse primer of the set M indicated in Table 4
[SEQ ID NO: 36]
GTCCACAAGCTTGGAGACTGTTTCAGAG Forward primer of the set O indicated in Table 4
[SEQ ID NO: 37]
TTTTAAGCTTCTCGTACCCCGCGTCTCAG Reverse primer of the set O indicated in Table 4
[SEQ ID NO: 38]
GTCCACAAGCTTGGAGACTGTTTCAGAG Forward primer of the set P indicated in Table 4
[SEQ ID NO: 39]
CACCCGAAGCTTCTCGTGTGAGCGCTGCG Reverse primer of the set P indicated in Table 4
[SEQ ID NO: 40]
GTCCACAAGCTTGGAGACTGTTTCAGAG Forward primer of the set Q indicated in Table 4
[SEQ ID NO: 41]
AGGTTAAGCTTGGTCCGTCAGTAGGCCAGTG Reverse primer of the set Q indicated in Table 4
[SEQ ID NO: 42]
GTCCACAAGCTTGGAGACTGTTTCAGAG Forward primer complementary to the base sequence of a
tetracycline resistance gene that pR6632 had
[SEQ ID NO: 43]
GTAACCAGCCAACTAATGAC Reverse primer complementary to the base sequence of a
tetracycline resistance gene that pR6632 had
[SEQ ID NO: 44]
CTCGTAATGGTTGTAGTTGC Remaining region deleting orf1 and orf2 regions
from replication region in pKR100
[SEQ ID NO: 45]
CGGTCAGGCTGGACGGTGCGTGGTCATAAACCGTGGGTCGGTTCGGAGAGCCGGGGGGTGGC

TTCCTATCGTCGTGAGATGAGCAGAGAACGCTATGAGCCGATGAGTGAGGCCCGGTTGGAAG

TCGCTTGGATGGTCGTGTTGCTGGGGTGTGCGCTGGTTCTTATGGGTGGGGTGGCCCTGGAT

GTGTTGATCGATCATCTCGCTGTCAGCTTCGCCTTGGCGGGGGTGCCGAGTGTGTTGGTGGT

GGCGGTGTTGTGGCGGCGGCACGTGCGCTAAGCCGTGTACGGGCACAGAAAAAGCCGGGTGG

TAGAGCCCGGCTTTTTCCGTGGGGGAGAGTCTCGTACCCCGCGTCTCAGTGTCCTGCACACC

GGTCGTGATGCCTACTGCCGCTACACGGAGCAAAGCTATGCGTTATGTGCCATAAACGCGGA

TCGCCCTTCGTCCAGCTCGTGGAGCTGGCTGAGTGCCTATGTGCCATAGGCGGGCGGGGGCA

CCCGAGCGGGCTCGTGTGAGCGCTGCGCTGGGCATAGGGAAGGCCGGGCGCTAGCCCAGCCC

TCCATGGGGGCAGAGGGCCCCGTGGTGTTGAGAGTGGCGAGCCCTACTGAGGGTCCTCGAAG

GCGTCGGGGCGCTTCGTGTCCTCTTCAGTTTTTGATCCCTGGCGTCCTGAACTTCGTTCGC

GACTGCCTCCGGGGTGCCGGTGGCAAGGAGAGCATGCAC

DNA-binding protein binding sequence 1
[SEQ ID NO: 46]
TCGGAGCTCCGA

-continued

DNA-binding protein binding sequence 2 [SEQ ID NO: 47]
TGATCGATCA

Repeat unit of repeat motif sequence 1 [SEQ ID NO: 48]
TGGCGTGGTCGTTG

Repeat unit of repeat motif sequence 2 [SEQ ID NO: 49]
GCGCTGGGGTG

Repeat unit of repeat motif sequence 3 [SEQ ID NO: 50]
TGGGGCTGTGGTGG

Repeat unit of repeat motif sequence 4 [SEQ ID NO: 51]
GCGGTGGTGTG

Repeat unit of repeat motif sequence 5 [SEQ ID NO: 52]
GGGCCGGGGTTG

Repeat unit of repeat motif sequence 6 [SEQ ID NO: 53]
GCCGGGGTTGT

Repeat unit of repeat motif sequence 7 [SEQ ID NO: 54]
TGGTCGTGTTG

Repeat unit of repeat motif sequence 8 [SEQ ID NO: 55]
TGTTGCTGGGGTG

Repeat unit of repeat motif sequence 9 [SEQ ID NO: 56]
TGGCGGTGTTGTGG

Repeat unit of repeat motif sequence 10 [SEQ ID NO: 57]
GGGGTGCCGGTGG

Oxidant sensitive sequence 1 [SEQ ID NO: 58]
TGTGGGGTGGCCCCTCAGCGAAATA

Oxidant sensitive sequence 2 [SEQ ID NO: 59]
GGCCTCTCAGC

Oxidant sensitive sequence 3 [SEQ ID NO: 60]
CTGCGGGCACCTCCTAC

Oxidant sensitive sequence 4 [SEQ ID NO: 61]
GGTGAGGGGTAACCC

Oxidant sensitive sequence 5 [SEQ ID NO: 62]
GTGGGGTGGC

Oxidant sensitive sequence 6 [SEQ ID NO: 63]
GGGGGGTGGCTTCCTATCG

Oxidant sensitive sequence 7 [SEQ ID NO: 64]
GTGGGGTGGCCC

Oxidant sensitive sequence 8 [SEQ ID NO: 65]
TGTGGCGGCGGCACGTGCGCTAA

Oxidant sensitive sequence 9 [SEQ ID NO: 66]
GCGGGGGCACCCGA

-continued

Oxidant sensitive sequence 10
[SEQ ID NO: 67]
CTGAGGGTCCTC

Inverted repeat sequence 1
[SEQ ID NO: 68]
GAAAAAGCCGGGCTGCTGCCCGGCTTTTTC

Inverted repeat sequence 2
[SEQ ID NO: 69]
CACAGAAAAAGCCGGGTGGTAGAGCCCGGCTTTTTCCGTG

INDUSTRIAL APPLICABILITY

The present invention can be used to introduce a useful gene into bacteria of the genus *Kocuria* that serve as host cells, thereby obtaining a transformant to which a useful biological function has been added. Such a transformant can further improve the original, high-level functions that the host cells have, such as organic solvent tolerance, heavy metal resistance, and proliferating ability, and may be used in an advantageous manner in various fields, such as food industry, production of fuel and pharmaceutical chemical products, and environmental cleanup.

The invention claimed is:

1. A circular plasmid that is autonomously replicable in bacteria, having a foreign gene and a replication region selected from the group consisting of:
  (i) the sequence of SEQ ID NO: 3;
  (ii) the sequence of position 559 to position 3170 of SEQ ID NO: 4;
  (iii) the sequence of position 312 to position 3170 of SEQ ID NO: 4;
  (iv) the sequence of position 7 to position 3170 of SEQ ID NO: 4;
  (v) the sequence of SEQ ID NO:4; and
  (vi) a sequence having 95% or more homology with any one of the sequences of (i) to (v).

2. The plasmid according to claim 1, wherein the bacteria are the bacteria of the genus *Kocuria*.

3. A transformant comprising the plasmid according to claim 1.

4. The plasmid according to claim 1, wherein the foreign gene is a drug resistance gene.

* * * * *

SEQUENCE LISTING

```
<160> NUMBER OF SEQ ID NOS: 70

<210> SEQ ID NO 1
<211> LENGTH: 213
<212> TYPE: DNA
<213> ORGANISM: Artificial sequence
<220> FEATURE:
<223> OTHER INFORMATION: Synthetic DNA fragment

<400> SEQUENCE: 1
atgggcgacc ctcagcttgt aatgggcttt ttccaggtct tccttcgtgc ctttctcgta      60
cagagcgtct gcttcgagaa gggcccattc cgcttcgaca aactgccggg caagaagttt     120
tttgctggat ggcttagtca tggcaaggaa cgtagctgcc gaagtagtga aggctgtaca     180
gatccgacgc ggttcgcgcg ggtccgtcag tag                                  213

<210> SEQ ID NO 2
<211> LENGTH: 1092
<212> TYPE: DNA
<213> ORGANISM: Artificial sequence
<220> FEATURE:
<223> OTHER INFORMATION: Synthetic DNA fragment

<400> SEQUENCE: 2
gtgaccagtg taggcacgca ccttccctcg tccaccagcc ccgccgcaac acggcaggcg      60
gctgttcggc aggcatttgt taaccattta ggcgtgcgcc acgtgcgtgt ggcggccacc     120
aagaacggtg cgccgcgcac cgttcccatt gaggcgttag gcgagttcgc cttttggacg     180
ccaccggcct ggcccaacct cggattgctg actattgacg tcgaccggga tgcggccgtg     240
ctcgagctct tcgccgcccc tgccctgccg catgtggtcg tggagacccc ccgcggggcc     300
caagcggtgt ggctgatcga ccgagtacac accggcccga acgccgccc gcacccgatc     360 gcctatgccg aaaccgtagg aagcgctttg cgtgcctccc tggatggaga ctcggccgtg     420
gatccattgc gcccggtacg tacccgtaac ccctgctaca gacctgcaca gcgcgatgtg     480
ttcaccactg cccgcccgct aacggcgccc taccgtctcg gagagctcca gaaatccctg     540
gatgctgctg gagcatggcc aacacgtcct gagcgctctc aggcccgtgg aagggcgcag     600
aaggccgttg acggagtgtt cgtgggccgt aacgacgccg tcaaccgctc cacctggctg     660
accgtgcgct acggactcga aaatggttcc gtgactcact ggaccgatgc cgacgtgctg     720
gagctggccc atggcattaa cgaggccgtc gctgctgagc aaggcgtgcc gcccttaccc     780
```

| | |
|---|---|
| gaggatcaag tgcgcgactt ggctgtctcg atctgccggc atcaacaccg acctggccgc | 840 |
| cgagccatct ccggacaagg ctcggccacc gcccgcgccc tcggcgctaa aggcggcgca | 900 |
| gcccgttccg aggccaaaac cattagcggg cggcgcaacg tgggcaaggc gaccgctgtg | 960 |
| cgttccgcat ccgcggcctt gcgttctgag agcatccgaa tcctggccga gcaagggcac | 1020 |
| acctacgagg ccattgccgc cgctgtcgga tgctccacta agaccgttca gcgtgctctt | 1080 |
| cgcgacctct ga | 1092 |

<210> SEQ ID NO 3
<211> LENGTH: 2140
<212> TYPE: DNA
<213> ORGANISM: Artificial sequence
<220> FEATURE:
<223> OTHER INFORMATION: Synthetic DNA fragment

<400> SEQUENCE: 3

| | |
|---|---|
| cggtcaggct ggacggtgcg tggtcataaa ccgtgggtcg gttcggagag ccgggggtg | 60 |
| gcttcctatc gtcgtgagat gagcagagaa cgctatgagc cgatgagtga ggcccggttg | 120 |
| gaagtcgctt ggatggtcgt gttgctgggg tgtgcgctgg ttcttatggg tggggtggcc | 180 |
| ctggatgtgt tgatcgatca tctcgctgtc agcttcgcct ggcgggggt gccgagtgtg | 240 |
| ttggtggtgg cggtgttgtg gcggcggcac gtgcgctaag ccgtgtacgg gcacagaaaa | 300 |
| agccgggtgg tagagcccgg cttttttccgt gggggagagt ctcgtacccc gcgtctcagt | 360 |
| gtcctgcaca ccggtcgtga tgcctactgc cgctacacgg agcaaagcta tgcgttatgt | 420 |
| gccataaacg cggatcgccc ttcgtccagc tcgtggagct ggctgagtgc ctatgtgcca | 480 |
| taggcgggcg ggggcacccg agcgggctcg tgtgagcgct gcgctgggca tagggaaggc | 540 |
| cgggcgctag cccagccctc catggggca gagggccccg tggtgttgag agtggcgagc | 600 |
| cctactgagg gtcctcgaag gcgtcggggg cgcttcgtgt cctcttcagt ttttgatccc | 660 |
| tggcgtcctg aacttcgttc gcgactgcct ccggggtgcc ggtggcaagg agagcatgca | 720 |
| catgggcgac cctcagcttg taatgggctt tttccaggtc ttccttcgtg cctttctcgt | 780 |
| acagagcgtc tgcttcgaga agggcccatt ccgcttcgac aaactgccgg gcaagaagtt | 840 |
| ttttgctgga tggcttagtc atggcaagga acgtagctgc cgaagtagtg aaggctgtac | 900 |
| agatccgacg cggttcgcgc gggtccgtca gtaggccagt gatgggccat agggtgacca | 960 |
| ggaaagagtt gagccccgga gattccaccc tccggggctc gacttccccg attgatagcg | 1020 |
| gcaatcagga gaagccttgt gaccagtgta ggcacgcacc ttccctcgtc caccagcccc | 1080 |
| gccgcaacac ggcaggcggc tgttcggcag gcatttgtta accatttagg cgtgcgccac | 1140 |
| gtgcgtgtgg cggccaccaa gaacggtgcg ccgcgcaccg ttcccattga ggcgttaggc | 1200 |
| gagttcgcct tttggacgcc accggcctgg cccaacctcg gattgctgac tattgacgtc | 1260 |
| gaccgggatg cggccgtgct cgagctcttc gccgcccctg ccctgccgca tgtggtcgtg | 1320 |
| gagacccccc gcgggccca gcggtgtgg ctgatcgacc gagtacacac cggcccgaac | 1380 |
| gcccgcccgc acccgatcgc ctatgccgaa accgtaggaa gcgctttgcg tgcctccctg | 1440 |
| gatggagact cggccgtgga tccattgcgc ccggtacgta cccgtaaccc ctgctacaga | 1500 |
| cctgcacagc gcgatgtgtt caccactgcc cgcccgctaa cggcgcccta ccgtctcgga | 1560 |
| gagctccaga aatccctgga tgctgctgga gcatggccaa cacgtcctga gcgctctcag | 1620 |
| gcccgtggaa gggcgcagaa ggccgttgac ggagtgttcg tgggccgtaa cgacgccgtc | 1680 |
| aaccgctcca cctggctgac cgtgcgctac ggactcgaaa atggttccgt gactcactgg | 1740 |

```
accgatgccg acgtgctgga gctggcccat ggcattaacg aggccgtcgc tgctgagcaa    1800
ggcgtgccgc ccttacccga ggatcaagtg cgcgacttgg ctgtctcgat ctgccggcat    1860
caacaccgac ctggccgccg agccatctcc ggacaaggct cggccaccgc ccgcgccctc    1920
ggcgctaaag gcggcgcagc ccgttccgag gccaaaacca ttagcgggcg cgcaacgtg     1980 ggcaaggcga ccgctgtgcg ttccgcatcc gcggccttgc gttctgagag catccgaatc    2040
ctggccgagc aagggcacac ctacgaggcc attgccgccg ctgtcggatg ctccactaag    2100
accgttcagc gtgctcttcg cgacctctga acagtctcc                          2140
```

<210> SEQ ID NO 4
<211> LENGTH: 3187
<212> TYPE: DNA
<213> ORGANISM: Artificial sequence
<220> FEATURE:
<223> OTHER INFORMATION: Synthetic DNA fragment

<400> SEQUENCE: 4

```
ataagcccaa ggtgagggga cgctccccgg gcctctcagc cccccctctg agggctcctg      60
cgggcacctc ctacgatcct ccgaacagcc ctgatcgtca cacctcatgc atcattcgat     120
gagccaggtc taggtgacca aacgcaggcg gccacagact cagctgcact ctcatcgtga     180
ggtgcccaga gcgtcgcaac aaggcaccga cccagcctca attttcatcc gccggcctta     240
acggcgaccg tcactgttga tgacttttgc tgtcctcgaa tcacccttcg cgggtgaggg     300
gtaacccgct tcgggtgagg caaccagaac gggtccctgt gctcggctat gtggtcgagc     360
aggtgcctgg tggggtggcg tggtcgttgt cggcgggccg gtttcgggcg cgctggggtg     420
acctagctgt gcgcaccgag gaccggtgcg aaggacaaga tgagcgtctt tcccgagggc     480
cggccaaaga atgcaagagg tgtgacgact tggatcagag ttcggagctc cgacgcattg     540
ggaggtgatt gggtgcagcg tgagaccagt ccgtagcgtt tgacgaatgc aaatgcgacg     600
cggggaccag gaggctagac atcgtcgaga tatggcttgg attctggtgc tgctggctgg     660
agtgcaggtg ggtttgctgg cgacggtgat cggtgtcttg gtcgaggacc tcgtggtggg     720
cactgtcgtt gctttggttc ctggggctgt ggtggtgggg ctgtggtggc ggcggttttt     780
ggactagccg gcgttgctgg gcatggaaaa agccgggctg ctgcccggct tttcttctg     840 ggaggcgggg cctggtcaac cgggcctccc gggaagcggt ggtgtgagca cgtcagttcc     900
cgcctccagt gttggccgtt cttcggttg ttcccaaaag tgacggcgat gggtgggtgg      960
aaggtcccgt ccaggtctga tttgccggca caggttgctg gccgggggtt gtccccgtag    1020
gggtctgtcc cggtcaggct ggacggtgcg tggtcataaa ccgtgggtcg gttcggagag    1080
ccggggggtg gcttcctatc gtcgtgagat gagcagagaa cgctatgagc cgatgagtga    1140
ggcccggttg gaagtcgctt ggatggtcgt gttgctgggg tgtgcgctgg ttcttatggg    1200
tggggtggcc ctggatgtgt tgatcgatca tctcgctgtc agcttcgcct tggcgggggt    1260
gccgagtgtg ttggtggtgg cggtgttgtg gcggcggcac gtgcgctaag ccgtgtacgg    1320
gcacagaaaa agccgggtgg tagagcccgg ctttttccgt gggggagagt ctcgtaccc     1380 gcgtctcagt gtcctgcaca ccggtcgtga tgcctactgc cgctacacgg agcaaagcta    1440
tgcgttatgt gccataaacg cggatcgccc ttcgtccagc tcgtggagct ggctgagtgc    1500
ctatgtgcca taggcgggcg ggggcacccg agcgggctcg tgtgagcgct gcgctgggca    1560
tagggaaggc cgggcgctag cccagccctc catgggggca gagggccccg tggtgttgag    1620
```

```
agtggcgagc cctactgagg gtcctcgaag gcgtcggggg cgcttcgtgt cctcttcagt    1680
ttttgatccc tggcgtcctg aacttcgttc gcgactgcct ccggggtgcc ggtggcaagg    1740
agagcatgca catgggcgac cctcagcttg taatgggctt tttccaggtc ttccttcgtg    1800
cctttctcgt acagagcgtc tgcttcgaga agggcccatt ccgcttcgac aaactgccgg    1860
gcaagaagtt ttttgctgga tggcttagtc atggcaagga acgtagctgc cgaagtagtg    1920
aaggctgtac agatccgacg cggttcgcgc gggtccgtca gtaggccagt gatgggccat    1980
agggtgacca ggaaagagtt gagccccgga gattccaccc tccggggctc gacttccccg    2040
attgatagcg gcaatcagga gaagccttgt gaccagtgta ggcacgcacc ttccctcgtc    2100
caccagcccc gccgcaacac ggcaggcggc tgttcggcag gcatttgtta accatttagg    2160
cgtgcgccac gtgcgtgtgg cggccaccaa gaacggtgcg ccgcgcaccg ttcccattga    2220
ggcgttaggc gagttcgcct tttggacgcc accggcctgg cccaacctcg gattgctgac    2280
tattgacgtc gaccgggatg cggccgtgct cgagctcttc gccgcccctg ccctgccgca    2340
tgtggtcgtg gagacccccc gcggggccca agcggtgtgg ctgatcgacc gagtacacac    2400
cggcccgaac gcccgcccgc acccgatcgc ctatgccgaa accgtaggaa gcgctttgcg    2460
tgcctccctg gatggagact cggccgtgga tccattgcgc ccggtacgta cccgtaaccc    2520
ctgctacaga cctgcacagc gcgatgtgtt caccactgcc cgcccgctaa cggcgcccta    2580
ccgtctcgga gagctccaga atccctgga tgctgctgga gcatggccaa cacgtcctga    2640
gcgctctcag gcccgtggaa gggcgcagaa ggccgttgac ggagtgttcg tgggccgtaa    2700
cgacgccgtc aaccgctcca cctggctgac cgtgcgctac ggactcgaaa atggttccgt    2760
gactcactgg accgatgccg acgtgctgga gctggcccat ggcattaacg aggccgtcgc    2820
tgctgagcaa ggcgtgccgc ccttacccga ggatcaagtg cgcgacttgg ctgtctcgat    2880
ctgccggcat caacaccgac ctggccgccg agccatctcc ggacaaggct cggccaccgc    2940
ccgcgccctc ggcgctaaag gcggcgcagc ccgttccgag gccaaaacca ttagcgggcg    3000
gcgcaacgtg ggcaaggcga ccgctgtgcg ttccgcatcc gcggccttgc gttctgagag    3060
catccgaatc ctggccgagc aagggcacac ctacgaggcc attgccgccg ctgtcggatg    3120
ctccactaag accgttcagc gtgctcttcg cgacctctga acagtctcc gtcgaggtgg    3180 acatttc                                                             3187
```

<210> SEQ ID NO 5
<211> LENGTH: 363
<212> TYPE: PRT
<213> ORGANISM: Artificial sequence
<220> FEATURE:
<223> OTHER INFORMATION: Synthetic protein

<400> SEQUENCE: 5

```
Met Thr Ser Val Gly Thr His Leu Pro Ser Ser Thr Ser Pro Ala Ala
1               5                   10                  15

Thr Arg Gln Ala Ala Val Arg Gln Ala Phe Val Asn His Leu Gly Val
            20                  25                  30

Arg His Val Arg Val Ala Ala Thr Lys Asn Gly Ala Pro Arg Thr Val
        35                  40                  45

Pro Ile Glu Ala Leu Gly Glu Phe Ala Phe Trp Thr Pro Pro Ala Trp
    50                  55                  60

Pro Asn Leu Gly Leu Leu Thr Ile Asp Val Asp Arg Asp Ala Ala Val
65                  70                  75                  80
```

-continued

```
Leu Glu Leu Phe Ala Ala Pro Ala Leu Pro His Val Val Glu Thr
                85                  90                  95

Pro Arg Gly Ala Gln Ala Val Trp Leu Ile Asp Arg Val His Thr Gly
            100                 105                 110

Pro Asn Ala Arg Pro His Pro Ile Ala Tyr Ala Glu Thr Val Gly Ser
            115                 120                 125

Ala Leu Arg Ala Ser Leu Asp Gly Asp Ser Ala Val Asp Pro Leu Arg
            130                 135                 140

Pro Val Arg Thr Arg Asn Pro Cys Tyr Arg Pro Ala Gln Arg Asp Val
145                 150                 155                 160

Phe Thr Thr Ala Arg Pro Leu Thr Ala Pro Tyr Arg Leu Gly Glu Leu
                165                 170                 175

Gln Lys Ser Leu Asp Ala Ala Gly Ala Trp Pro Thr Arg Pro Glu Arg
            180                 185                 190

Ser Gln Ala Arg Gly Arg Ala Gln Lys Ala Val Asp Gly Val Phe Val
            195                 200                 205

Gly Arg Asn Asp Ala Val Asn Arg Ser Thr Trp Leu Thr Val Arg Tyr
210                 215                 220

Gly Leu Glu Asn Gly Ser Val Thr His Trp Thr Asp Ala Asp Val Leu
225                 230                 235                 240

Glu Leu Ala His Gly Ile Asn Glu Ala Val Ala Ala Glu Gln Gly Val
                245                 250                 255

Pro Pro Leu Pro Glu Asp Gln Val Arg Asp Leu Ala Val Ser Ile Cys
            260                 265                 270

Arg His Gln His Arg Pro Gly Arg Arg Ala Ile Ser Gly Gln Gly Ser
            275                 280                 285

Ala Thr Ala Arg Ala Leu Gly Ala Lys Gly Gly Ala Ala Arg Ser Glu
290                 295                 300

Ala Lys Thr Ile Ser Gly Arg Arg Asn Val Gly Lys Ala Thr Ala Val
305                 310                 315                 320

Arg Ser Ala Ser Ala Ala Leu Arg Ser Glu Ser Ile Arg Ile Leu Ala
                325                 330                 335

Glu Gln Gly His Thr Tyr Glu Ala Ile Ala Ala Ala Val Gly Cys Ser
            340                 345                 350

Thr Lys Thr Val Gln Arg Ala Leu Arg Asp Leu
            355                 360

<210> SEQ ID NO 6
<211> LENGTH: 70
<212> TYPE: PRT
<213> ORGANISM: Artificial sequence
<220> FEATURE:
<223> OTHER INFORMATION: Synthetic protein

<400> SEQUENCE: 6

Met Gly Asp Pro Gln Leu Val Met Gly Phe Phe Gln Val Phe Leu Arg
1               5                   10                  15

Ala Phe Leu Val Gln Ser Val Cys Phe Glu Lys Gly Pro Phe Arg Phe
                20                  25                  30

Asp Lys Leu Pro Gly Lys Lys Phe Phe Ala Gly Trp Leu Ser His Gly
            35                  40                  45

Lys Glu Arg Ser Cys Arg Ser Ser Glu Gly Cys Thr Asp Pro Thr Arg
        50                  55                  60

Phe Ala Arg Val Arg Gln
65                  70
```

<210> SEQ ID NO 7
<211> LENGTH: 20
<212> TYPE: DNA
<213> ORGANISM: Artificial sequence
<220> FEATURE:
<223> OTHER INFORMATION: Synthetic DNA fragment

<400> SEQUENCE: 7
agagtttgat cctggctcag                                               20

<210> SEQ ID NO 8
<211> LENGTH: 18
<212> TYPE: DNA
<213> ORGANISM: Artificial sequence
<220> FEATURE:
<223> OTHER INFORMATION: Synthetic DNA fragment

<400> SEQUENCE: 8
aaaggaggtg atccagcc                                                 18

<210> SEQ ID NO 9
<211> LENGTH: 16
<212> TYPE: DNA
<213> ORGANISM: Artificial sequence
<220> FEATURE:
<223> OTHER INFORMATION: Synthetic DNA fragment

<400> SEQUENCE: 9
tggtggcggt gttgtg                                                   16

<210> SEQ ID NO 10
<211> LENGTH: 18
<212> TYPE: DNA
<213> ORGANISM: Artificial sequence
<220> FEATURE:
<223> OTHER INFORMATION: Synthetic DNA fragment

<400> SEQUENCE: 10
tcgcgaacga agttcagg                                                 18

<210> SEQ ID NO 11
<211> LENGTH: 37
<212> TYPE: DNA
<213> ORGANISM: Artificial sequence
<220> FEATURE:
<223> OTHER INFORMATION: Synthetic DNA fragment

<400> SEQUENCE: 11
gccggtggca aggagagcat gcacatgggc gaccctc                            37

<210> SEQ ID NO 12
<211> LENGTH: 20
<212> TYPE: DNA
<213> ORGANISM: Artificial sequence
<220> FEATURE:
<223> OTHER INFORMATION: Synthetic DNA fragment

<400> SEQUENCE: 12
cactggccta ctgacggacc                                               20

<210> SEQ ID NO 13
<211> LENGTH: 20
<212> TYPE: DNA
<213> ORGANISM: Artificial sequence
<220> FEATURE:
<223> OTHER INFORMATION: Synthetic DNA fragment

```
<400> SEQUENCE: 13
ggtccgtcag taggccagtg                                               20

<210> SEQ ID NO 14
<211> LENGTH: 16
<212> TYPE: DNA
<213> ORGANISM: Artificial sequence
<220> FEATURE:
<223> OTHER INFORMATION: Synthetic DNA fragment

<400> SEQUENCE: 14
ggagactgtt tcagag                                                   16

<210> SEQ ID NO 15
<211> LENGTH: 16
<212> TYPE: DNA
<213> ORGANISM: Artificial sequence
<220> FEATURE:
<223> OTHER INFORMATION: Synthetic DNA fragment

<400> SEQUENCE: 15
tggtggcggt gttgtg                                                   16

<210> SEQ ID NO 16
<211> LENGTH: 20
<212> TYPE: DNA
<213> ORGANISM: Artificial sequence
<220> FEATURE:
<223> OTHER INFORMATION: Synthetic DNA fragment

<400> SEQUENCE: 16
cactggccta ctgacggacc                                               20

<210> SEQ ID NO 17
<211> LENGTH: 37
<212> TYPE: DNA
<213> ORGANISM: Artificial sequence
<220> FEATURE:
<223> OTHER INFORMATION: Synthetic DNA fragment

<400> SEQUENCE: 17
gccggtggca aggagagcat gcacatgggc gaccctc                            37

<210> SEQ ID NO 18
<211> LENGTH: 16
<212> TYPE: DNA
<213> ORGANISM: Artificial sequence
<220> FEATURE:
<223> OTHER INFORMATION: Synthetic DNA fragment

<400> SEQUENCE: 18
ggagactgtt tcagag                                                   16

<210> SEQ ID NO 19
<211> LENGTH: 16
<212> TYPE: DNA
<213> ORGANISM: Artificial sequence
<220> FEATURE:
<223> OTHER INFORMATION: Synthetic DNA fragment

<400> SEQUENCE: 19
tggtggcggt gttgtg                                                   16

<210> SEQ ID NO 20
```

```
<211> LENGTH: 16
<212> TYPE: DNA
<213> ORGANISM: Artificial sequence
<220> FEATURE:
<223> OTHER INFORMATION: Synthetic DNA fragment

<400> SEQUENCE: 20
ggagactgtt tcagag                                                    16

<210> SEQ ID NO 21
<211> LENGTH: 20
<212> TYPE: DNA
<213> ORGANISM: Artificial sequence
<220> FEATURE:
<223> OTHER INFORMATION: Synthetic DNA fragment

<400> SEQUENCE: 21
gttacaatag cgacggagag                                                20

<210> SEQ ID NO 22
<211> LENGTH: 22
<212> TYPE: DNA
<213> ORGANISM: Artificial sequence
<220> FEATURE:
<223> OTHER INFORMATION: Synthetic DNA fragment

<400> SEQUENCE: 22
aggttagtga cattagaaaa cc                                             22

<210> SEQ ID NO 23
<211> LENGTH: 27
<212> TYPE: DNA
<213> ORGANISM: Artificial sequence
<220> FEATURE:
<223> OTHER INFORMATION: Synthetic DNA fragment

<400> SEQUENCE: 23
attaaagctt ccaaggtgag gggacgc                                        27

<210> SEQ ID NO 24
<211> LENGTH: 28
<212> TYPE: DNA
<213> ORGANISM: Artificial sequence
<220> FEATURE:
<223> OTHER INFORMATION: Synthetic DNA fragment

<400> SEQUENCE: 24
gtccacaagc ttggagactg tttcagag                                       28

<210> SEQ ID NO 25
<211> LENGTH: 27
<212> TYPE: DNA
<213> ORGANISM: Artificial sequence
<220> FEATURE:
<223> OTHER INFORMATION: Synthetic DNA fragment

<400> SEQUENCE: 25
attaaagctt ccaaggtgag gggacgc                                        27

<210> SEQ ID NO 26
<211> LENGTH: 34
<212> TYPE: DNA
<213> ORGANISM: Artificial sequence
<220> FEATURE:
<223> OTHER INFORMATION: Synthetic DNA fragment

<400> SEQUENCE: 26
```

```
aaaaaagctt cggcggccag gtcggtgttg atgc                                    34

<210> SEQ ID NO 27
<211> LENGTH: 29
<212> TYPE: DNA
<213> ORGANISM: Artificial sequence
<220> FEATURE:
<223> OTHER INFORMATION: Synthetic DNA fragment

<400> SEQUENCE: 27
ttttaagctt cgggtgaggc aaccagaac                                          29

<210> SEQ ID NO 28
<211> LENGTH: 28
<212> TYPE: DNA
<213> ORGANISM: Artificial sequence
<220> FEATURE:
<223> OTHER INFORMATION: Synthetic DNA fragment

<400> SEQUENCE: 28
gtccacaagc ttggagactg tttcagag                                           28

<210> SEQ ID NO 29
<211> LENGTH: 25
<212> TYPE: DNA
<213> ORGANISM: Artificial sequence
<220> FEATURE:
<223> OTHER INFORMATION: Synthetic DNA fragment

<400> SEQUENCE: 29
attggaagct tcgtgagacc agtcc                                              25

<210> SEQ ID NO 30
<211> LENGTH: 28
<212> TYPE: DNA
<213> ORGANISM: Artificial sequence
<220> FEATURE:
<223> OTHER INFORMATION: Synthetic DNA fragment

<400> SEQUENCE: 30
gtccacaagc ttggagactg tttcagag                                           28

<210> SEQ ID NO 31
<211> LENGTH: 27
<212> TYPE: DNA
<213> ORGANISM: Artificial sequence
<220> FEATURE:
<223> OTHER INFORMATION: Synthetic DNA fragment

<400> SEQUENCE: 31
ttttaagctt ggactagccg gcgttgc                                            27

<210> SEQ ID NO 32
<211> LENGTH: 28
<212> TYPE: DNA
<213> ORGANISM: Artificial sequence
<220> FEATURE:
<223> OTHER INFORMATION: Synthetic DNA fragment

<400> SEQUENCE: 32
gtccacaagc ttggagactg tttcagag                                           28

<210> SEQ ID NO 33
<211> LENGTH: 35
<212> TYPE: DNA
```

```
<213> ORGANISM: Artificial sequence
<220> FEATURE:
<223> OTHER INFORMATION: Synthetic DNA fragment

<400> SEQUENCE: 33
aagggtaagc ttcggtcagg ctggacggtg cgtgg                              35

<210> SEQ ID NO 34
<211> LENGTH: 28
<212> TYPE: DNA
<213> ORGANISM: Artificial sequence
<220> FEATURE:
<223> OTHER INFORMATION: Synthetic DNA fragment

<400> SEQUENCE: 34
gtccacaagc ttggagactg tttcagag                                      28

<210> SEQ ID NO 35
<211> LENGTH: 29
<212> TYPE: DNA
<213> ORGANISM: Artificial sequence
<220> FEATURE:
<223> OTHER INFORMATION: Synthetic DNA fragment

<400> SEQUENCE: 35
aaggaagctt gtgcgctaag ccgtgtacg                                     29

<210> SEQ ID NO 36
<211> LENGTH: 28
<212> TYPE: DNA
<213> ORGANISM: Artificial sequence
<220> FEATURE:
<223> OTHER INFORMATION: Synthetic DNA fragment

<400> SEQUENCE: 36
gtccacaagc ttggagactg tttcagag                                      28

<210> SEQ ID NO 37
<211> LENGTH: 29
<212> TYPE: DNA
<213> ORGANISM: Artificial sequence
<220> FEATURE:
<223> OTHER INFORMATION: Synthetic DNA fragment

<400> SEQUENCE: 37
ttttaagctt ctcgtacccc gcgtctcag                                     29

<210> SEQ ID NO 38
<211> LENGTH: 28
<212> TYPE: DNA
<213> ORGANISM: Artificial sequence
<220> FEATURE:
<223> OTHER INFORMATION: Synthetic DNA fragment

<400> SEQUENCE: 38
gtccacaagc ttggagactg tttcagag                                      28

<210> SEQ ID NO 39
<211> LENGTH: 29
<212> TYPE: DNA
<213> ORGANISM: Artificial sequence
<220> FEATURE:
<223> OTHER INFORMATION: Synthetic DNA fragment

<400> SEQUENCE: 39
cacccgaagc ttctcgtgtg agcgctgcg                                     29
```

<210> SEQ ID NO 40
<211> LENGTH: 28
<212> TYPE: DNA
<213> ORGANISM: Artificial sequence
<220> FEATURE:
<223> OTHER INFORMATION: Synthetic DNA fragment

<400> SEQUENCE: 40
gtccacaagc ttggagactg tttcagag                                       28

<210> SEQ ID NO 41
<211> LENGTH: 31
<212> TYPE: DNA
<213> ORGANISM: Artificial sequence
<220> FEATURE:
<223> OTHER INFORMATION: Synthetic DNA fragment

<400> SEQUENCE: 41
aggttaagct tggtccgtca gtaggccagt g                                   31

<210> SEQ ID NO 42
<211> LENGTH: 28
<212> TYPE: DNA
<213> ORGANISM: Artificial sequence
<220> FEATURE:
<223> OTHER INFORMATION: Synthetic DNA fragment

<400> SEQUENCE: 42
gtccacaagc ttggagactg tttcagag                                       28

<210> SEQ ID NO 43
<211> LENGTH: 20
<212> TYPE: DNA
<213> ORGANISM: Artificial sequence
<220> FEATURE:
<223> OTHER INFORMATION: Synthetic DNA fragment

<400> SEQUENCE: 43
gtaaccagcc aactaatgac                                                20

<210> SEQ ID NO 44
<211> LENGTH: 20
<212> TYPE: DNA
<213> ORGANISM: Artificial sequence
<220> FEATURE:
<223> OTHER INFORMATION: Synthetic DNA fragment

<400> SEQUENCE: 44
ctcgtaatgg ttgtagttgc                                                20

<210> SEQ ID NO 45
<211> LENGTH: 721
<212> TYPE: DNA
<213> ORGANISM: Artificial sequence
<220> FEATURE:
<223> OTHER INFORMATION: Synthetic DNA fragment

<400> SEQUENCE: 45
cggtcaggct ggacggtgcg tggtcataaa ccgtgggtcg gttcggagag ccgggggtg      60 gcttcctatc gtcgtgagat gagcagagaa cgctatgagc cgatgagtga ggcccggttg    120
gaagtcgctt ggatggtcgt gttgctgggg tgtgcgctgg ttcttatggg tggggtggcc    180
ctggatgtgt tgatcgatca tctcgctgtc agcttcgcct tggcgggggt gccgagtgtg    240

```
ttggtggtgg cggtgttgtg gcggcggcac gtgcgctaag ccgtgtacgg gcacagaaaa    300
agccgggtgg tagagcccgg cttttttccgt gggggagagt ctcgtacccc gcgtctcagt   360
gtcctgcaca ccggtcgtga tgcctactgc cgctacacgg agcaaagcta tgcgttatgt    420
gccataaacg cggatcgccc ttcgtccagc tcgtggagct ggctgagtgc ctatgtgcca    480
taggcgggcg ggggcacccg agcgggctcg tgtgagcgct gcgctgggca tagggaaggc    540
cgggcgctag cccagccctc catgggggca gagggcccccg tggtgttgag agtggcgagc   600
cctactgagg gtcctcgaag gcgtcggggg cgcttcgtgt cctcttcagt ttttgatccc    660
tggcgtcctg aacttcgttc gcgactgcct ccggggtgcc ggtggcaagg agagcatgca    720
c                                                                    721
```

<210> SEQ ID NO 46
<211> LENGTH: 12
<212> TYPE: DNA
<213> ORGANISM: Artificial sequence
<220> FEATURE:
<223> OTHER INFORMATION: Synthetic DNA fragment

<400> SEQUENCE: 46

```
tcggagctcc ga                                                         12
```

<210> SEQ ID NO 47
<211> LENGTH: 10
<212> TYPE: DNA
<213> ORGANISM: Artificial sequence
<220> FEATURE:
<223> OTHER INFORMATION: Synthetic DNA fragment

<400> SEQUENCE: 47

```
tgatcgatca                                                            10
```

<210> SEQ ID NO 48
<211> LENGTH: 14
<212> TYPE: DNA
<213> ORGANISM: Artificial sequence
<220> FEATURE:
<223> OTHER INFORMATION: Synthetic DNA fragment

<400> SEQUENCE: 48

```
tggcgtggtc gttg                                                       14
```

<210> SEQ ID NO 49
<211> LENGTH: 11
<212> TYPE: DNA
<213> ORGANISM: Artificial sequence
<220> FEATURE:
<223> OTHER INFORMATION: Synthetic DNA fragment

<400> SEQUENCE: 49

```
gcgctggggt g                                                          11
```

<210> SEQ ID NO 50
<211> LENGTH: 14
<212> TYPE: DNA
<213> ORGANISM: Artificial sequence
<220> FEATURE:
<223> OTHER INFORMATION: Synthetic DNA fragment

<400> SEQUENCE: 50

```
tggggctgtg gtgg                                                       14
```

```
<210> SEQ ID NO 51
<211> LENGTH: 11
<212> TYPE: DNA
<213> ORGANISM: Artificial sequence
<220> FEATURE:
<223> OTHER INFORMATION: Synthetic DNA fragment

<400> SEQUENCE: 51
gcggtggtgt g                                                              11

<210> SEQ ID NO 52
<211> LENGTH: 12
<212> TYPE: DNA
<213> ORGANISM: Artificial sequence
<220> FEATURE:
<223> OTHER INFORMATION: Synthetic DNA fragment

<400> SEQUENCE: 52
gggccggggt tg                                                             12

<210> SEQ ID NO 53
<211> LENGTH: 11
<212> TYPE: DNA
<213> ORGANISM: Artificial sequence
<220> FEATURE:
<223> OTHER INFORMATION: Synthetic DNA fragment

<400> SEQUENCE: 53
gccggggttg t                                                              11

<210> SEQ ID NO 54
<211> LENGTH: 11
<212> TYPE: DNA
<213> ORGANISM: Artificial sequence
<220> FEATURE:
<223> OTHER INFORMATION: Synthetic DNA fragment

<400> SEQUENCE: 54
tggtcgtgtt g                                                              11

<210> SEQ ID NO 55
<211> LENGTH: 13
<212> TYPE: DNA
<213> ORGANISM: Artificial sequence
<220> FEATURE:
<223> OTHER INFORMATION: Synthetic DNA fragment

<400> SEQUENCE: 55
tgttgctggg gtg                                                            13

<210> SEQ ID NO 56
<211> LENGTH: 14
<212> TYPE: DNA
<213> ORGANISM: Artificial sequence
<220> FEATURE:
<223> OTHER INFORMATION: Synthetic DNA fragment

<400> SEQUENCE: 56
tggcggtgtt gtgg                                                           14

<210> SEQ ID NO 57
<211> LENGTH: 13
<212> TYPE: DNA
<213> ORGANISM: Artificial sequence
<220> FEATURE:
<223> OTHER INFORMATION: Synthetic DNA fragment
```

```
<400> SEQUENCE: 57
ggggtgccgg tgg                                                              13

<210> SEQ ID NO 58
<211> LENGTH: 25
<212> TYPE: DNA
<213> ORGANISM: Artificial sequence
<220> FEATURE:
<223> OTHER INFORMATION: Synthetic DNA fragment

<400> SEQUENCE: 58
tgtggggtgg ccctcagcg aaata                                                  25

<210> SEQ ID NO 59
<211> LENGTH: 11
<212> TYPE: DNA
<213> ORGANISM: Artificial sequence
<220> FEATURE:
<223> OTHER INFORMATION: Synthetic DNA fragment

<400> SEQUENCE: 59
ggcctctcag c                                                                11

<210> SEQ ID NO 60
<211> LENGTH: 17
<212> TYPE: DNA
<213> ORGANISM: Artificial sequence
<220> FEATURE:
<223> OTHER INFORMATION: Synthetic DNA fragment

<400> SEQUENCE: 60
ctgcgggcac ctcctac                                                          17

<210> SEQ ID NO 61
<211> LENGTH: 15
<212> TYPE: DNA
<213> ORGANISM: Artificial sequence
<220> FEATURE:
<223> OTHER INFORMATION: Synthetic DNA fragment

<400> SEQUENCE: 61
ggtgaggggt aaccc                                                            15

<210> SEQ ID NO 62
<211> LENGTH: 10
<212> TYPE: DNA
<213> ORGANISM: Artificial sequence
<220> FEATURE:
<223> OTHER INFORMATION: Synthetic DNA fragment

<400> SEQUENCE: 62
gtggggtggc                                                                  10

<210> SEQ ID NO 63
<211> LENGTH: 19
<212> TYPE: DNA
<213> ORGANISM: Artificial sequence
<220> FEATURE:
<223> OTHER INFORMATION: Synthetic DNA fragment

<400> SEQUENCE: 63 gggggggtggc ttcctatcg                                                       19

<210> SEQ ID NO 64
<211> LENGTH: 12
```

```
<212> TYPE: DNA
<213> ORGANISM: Artificial sequence
<220> FEATURE:
<223> OTHER INFORMATION: Synthetic DNA fragment

<400> SEQUENCE: 64
gtggggtggc cc                                                             12

<210> SEQ ID NO 65
<211> LENGTH: 23
<212> TYPE: DNA
<213> ORGANISM: Artificial sequence
<220> FEATURE:
<223> OTHER INFORMATION: Synthetic DNA fragment

<400> SEQUENCE: 65
tgtggcggcg gcacgtgcgc taa                                                 23

<210> SEQ ID NO 66
<211> LENGTH: 14
<212> TYPE: DNA
<213> ORGANISM: Artificial sequence
<220> FEATURE:
<223> OTHER INFORMATION: Synthetic DNA fragment

<400> SEQUENCE: 66 gcggggcac ccga                                                            14

<210> SEQ ID NO 67
<211> LENGTH: 12
<212> TYPE: DNA
<213> ORGANISM: Artificial sequence
<220> FEATURE:
<223> OTHER INFORMATION: Synthetic DNA fragment

<400> SEQUENCE: 67
ctgagggtcc tc                                                             12

<210> SEQ ID NO 68
<211> LENGTH: 30
<212> TYPE: DNA
<213> ORGANISM: Artificial sequence
<220> FEATURE:
<223> OTHER INFORMATION: Synthetic DNA fragment

<400> SEQUENCE: 68
gaaaaagccg ggctgctgcc cggcttttc                                           30

<210> SEQ ID NO 69
<211> LENGTH: 40
<212> TYPE: DNA
<213> ORGANISM: Artificial sequence
<220> FEATURE:
<223> OTHER INFORMATION: Synthetic DNA fragment

<400> SEQUENCE: 69
cacagaaaaa gccgggtggt agagcccggc tttttccgtg                               40

<210> SEQ ID NO 70
<211> LENGTH: 917
<212> TYPE: DNA
<213> ORGANISM: Actinosynnema mirum DSM 43827

<400> SEQUENCE: 70
acgtcgccgc gctcgtcccg tccgggttcg gctccgcctc gctcgtgccc gccgcgttcg         60
```

```
                                                          -continued gcgtctccgc actcgccacc gacctggatc ccgcagacct cgaccccgcc gccctggacc      120
ccgccgaggt cgccgggctc gccgcgcccg agctggggga gctgctgcgc ctgcgcctgc      180
gggtccgacc cggcgcggcc gaggtggtgc gggcgaccgc cgtcctcggc gaggacgcca      240
ccgtcgaccg ggtcgccgag ctggcaggcg tcgagcaccg cgaggtgctc gccctggtcg      300
acgccctggt ccggctgcgc ctgctccgcg acggcacccc gctcgccttc aaccacccct      360
acctgcgggc ctgcgtgctc gccgacctgc cggtcgccac ccgcgccgcc gaccacgccc      420
gcgccgcctc ggcgctcgcc gaggccgggg aaccggccag gcgggtcgcc gcgcacctgc      480
gccaggccca cgacgtgccg ctgccctggg gcgtcccggt gctgcgcgag gccgcccgct      540
cggcgctgcg cgcgggcgac ccggccgagg cccgcgcctg tctggagcgc gcgctgcggg      600
agcgcgccgc gcccgccgag cgcctgggcg cgcgcctgga gctggtgcac gcggtgttcc      660
tcgccgaccc ggccgagggc gcgtcgctgc tgcgcgagag cctcgtcctc gccgacgaca      720
ccggcctggc cgccgaccag gccgcccagc tgctgctgcg gctgtgccgc ccggtcgacg      780
cccggttcgc cctcgccctc ggcccgcagc tggtcgccag gctcggcccc gccgaccacg      840
accgctcgtg gcggctgcgc gccctgtgct tcctcgcggg cgcgggcaac aaccccggcc      900
tggcgctgcg cgcgggc                                                    917
```